US009629848B2

(12) United States Patent
Eisenbarth et al.

(10) Patent No.: US 9,629,848 B2
(45) Date of Patent: Apr. 25, 2017

(54) COMPOUNDS THAT MODULATE AUTOIMMUNITY AND METHODS OF USING THE SAME

(75) Inventors: George Eisenbarth, Golden, CO (US); Aaron Michels, Aurora, CO (US); Maki Nakayama, Denver, CO (US); David Ostrov, Gainesville, FL (US)

(73) Assignees: The Regents of the University of Colorado, a body corporate, Denver, CO (US); The University of Florida Research Foundation Incorporated, Gainesville, FL (US)

( * ) Notice: Subject to any disclaimer, the term of this patent is extended or adjusted under 35 U.S.C. 154(b) by 51 days.

(21) Appl. No.: 14/119,926

(22) PCT Filed: May 29, 2012
(Under 37 CFR 1.47)

(86) PCT No.: PCT/US2012/039849
§ 371 (c)(1),
(2), (4) Date: Jul. 28, 2014

(87) PCT Pub. No.: WO2012/162697
PCT Pub. Date: Nov. 29, 2012

(65) Prior Publication Data
US 2015/0038480 A1 Feb. 5, 2015

Related U.S. Application Data

(60) Provisional application No. 61/490,417, filed on May 26, 2011, provisional application No. 61/580,188, filed on Dec. 23, 2011.

(51) Int. Cl.
| | | |
|---|---|---|
| *A61K 31/53* | (2006.01) | |
| *A61K 31/519* | (2006.01) | |
| *A61K 31/221* | (2006.01) | |
| *A61K 31/4409* | (2006.01) | |
| *A61K 31/4164* | (2006.01) | |
| *A61K 31/495* | (2006.01) | |
| *A61K 31/397* | (2006.01) | |
| *A61K 31/155* | (2006.01) | |
| *A61K 31/195* | (2006.01) | |
| *A61K 31/34* | (2006.01) | |
| *A61K 31/427* | (2006.01) | |
| *A61K 45/06* | (2006.01) | |
| *A61K 31/64* | (2006.01) | |

(52) U.S. Cl.
CPC ............ *A61K 31/53* (2013.01); *A61K 31/155* (2013.01); *A61K 31/195* (2013.01); *A61K 31/221* (2013.01); *A61K 31/397* (2013.01); *A61K 31/4164* (2013.01); *A61K 31/427* (2013.01); *A61K 31/4409* (2013.01); *A61K 31/495* (2013.01); *A61K 31/519* (2013.01); *A61K 31/64* (2013.01); *A61K 45/06* (2013.01)

(58) Field of Classification Search
CPC .. A61K 31/53; A61K 31/221; A61K 31/4409; A61K 31/4164; A61K 31/519; A61K 31/495; A61K 31/397; A61K 31/427; A61K 45/06; A61K 31/195; A61K 31/64; A61K 31/155
See application file for complete search history.

(56) References Cited

U.S. PATENT DOCUMENTS

| | | | |
|---|---|---|---|
| 4,691,018 | A | 9/1987 | Mori et al. |
| 5,475,033 | A | 12/1995 | Ohmori et al. |
| 5,594,100 | A | 1/1997 | Wegman |
| 7,144,569 | B1 | 12/2006 | Anderson et al. |
| 7,749,503 | B2 | 7/2010 | Tobia et al. |
| 8,314,210 | B2 | 11/2012 | Wucherpfennig et al. |
| 2002/0150914 | A1 | 10/2002 | Andersen et al. |
| 2004/0096734 | A1 | 5/2004 | Calundann et al. |
| 2004/0137514 | A1 | 7/2004 | Steenbakkers |
| 2004/0265327 | A1 | 12/2004 | Grassetti et al. |
| 2007/0021341 | A1 | 1/2007 | Sela et al. |
| 2007/0196369 | A1 | 8/2007 | Hoogenboom et al. |
| 2008/0194462 | A1 | 8/2008 | Wucherpfennig et al. |
| 2008/0214656 | A1 | 9/2008 | Lim et al. |
| 2012/0171212 | A1 | 7/2012 | Eisenbarth et al. |
| 2012/0195929 | A1 | 8/2012 | Eisenbarth et al. |

FOREIGN PATENT DOCUMENTS

| | | |
|---|---|---|
| WO | WO 03/070752 | 8/2003 |
| WO | WO 2004/007528 | 1/2004 |
| WO | WO 2010/141883 | 12/2010 |

OTHER PUBLICATIONS

Hurtenbach, U., "Prevention of autoimmune diabetes in non-obese diabetic mice by treatment with a class II major histocompatibility complex-blocking peptide." The Journal of experimental medicine 177.5 (1993): 1499-1504.*
Lee, K.h., "Structure of a human insulin peptide—HLA-DQ8 complex and susceptibility to type 1 diabetes." Nature immunology 2.6 (2001): 501-507.*
Kachapati, K.,"The non-obese diabetic (NOD) mouse as a model of human type 1 diabetes." Animal Models in Diabetes Research. Humana Press, 2012. 3-16.*
WebMD 2014 Diabetes Mellitus: Types, Symptoms, Causes, Treatments; accessed online Oct. 27, 2015; http://www.webmd.com/diabetes/guide/types-of-diabetes-mellitus, p. 1-7.*
Scheen, A. J.,"Pathophysiology of type 2 diabetes." Acta Clinica Belgica 58.6 (2003): 335-341.*

(Continued)

*Primary Examiner* — Samantha Shterengarts
*Assistant Examiner* — Matt Mauro
(74) *Attorney, Agent, or Firm* — Sheridan Ross P.C.

(57) ABSTRACT

The invention provides methods of preventing, treating or ameliorating autoimmune diseases, such as diabetes and celiac disease, by decreasing the binding of MHC class II molecules to antigenic peptides or fragments of antigenic peptides of the autoimmune disease by the administration of small organic compounds. The invention also provides pharmaceutical compositions comprising the therapeutically effective small organic compounds and methods of using the same.

3 Claims, 17 Drawing Sheets

(56) References Cited

OTHER PUBLICATIONS

"NSC10408—Compound Summary" PubChem Compound, create date Mar. 27, 2005, 5 pages, [retrieved Aug. 24, 2012 from pubchem.ncbi.nlm.nih.gov/summary/summary.cgi?cid=407900].

Li et al. "A computer screening approach to immunoglobulin superfamily structures and interactions: Discovery of small non-peptidic CD4 inhibitors as novel immunotherapeutics," Proceedings of the National Academy of Sciences, Jan. 1997, vol. 94, No. 1, pp. 73-78.

Salvati et al. "Recombinant human interleukin 10 suppresses gliadin dependent T cell activation in ex vivo cultured coeliac intestinal mucosa," GUT, Jan. 2005, vol. 54, No. 1, pp. 46-53.

Wucherpfennig "Insights into autoimmunity gained from structural analysis of MHC-peptide complexes," Current Opinion in Immunology, Dec. 2001, vol. 13, No. 6, pp. 650-656.

International Search Report and Written Opinion for International (PCT) Patent Application No. PCT/US12/39849, mailed Sep. 12, 2012 9 pages.

International Preliminary Report on Patentability for International (PCT) Patent Application No. PCT/US2012/039849, mailed Dec. 5, 2013 7 pages.

Aharoni et al., "Immunomodulation of experimental allergic encephalomyelitis by antibodies to the antigen-la complex," Nature, 1991, vol. 351, pp. 147-150.

Aoki et al., "NOD mice and autoimmunity," Autoimmun. Rev., 2005, vol. 4, pp. 373-379.

Boulard et al., "An interval tightly linked to but distinct from the h2 complex controls both overt diabetes (iddl6) and chronic experimental autoimmune thyroiditis (ceatl) in nonobese diabetic mice," Diabetes, 2002, vol. 51, pp. 2141-2147.

Chung et al., "Competitive Inhibition In Vivo and Skewing of the T Cell Repertoire of Antigen-Specific CTL Priming by an Anti-Peptide-MHC Monoclonal Antibody," J. Immunol., 2001, vol. 167, pp. 699-707.

Corper et al., "A structural framework for deciphering the link between I-Ag7 and autoimmune diabetes," Science, 2000, vol. 288, pp. 505-511.

Crawford et al., "Mimotopes for Alloreactive and Conventional T Cells in a Peptide-MHC Display Library," PLoS. Biol., 2004, vol. 2, p. 0523-0533.

Faideau et al., "Expression of preproinsulin-2 gene shapes the immune response to preproinsulin in normal mice," J. Immunol., 2004, vol. 172, pp. 25-33.

Fairbrother et al., "Effects of Three Plant Growth Regulators on the Immune Response of Young and Aged Deer Mice Peromyscus Maniculatus," Arch. Environ. Contam, Toxicol., 1986, vol. 15, pp. 265-275.

Fife et al., "Insulin-induced remission in new-onset NOD mice is maintained by the PD-1-PD-L1 pathway," J. Experimental Med., 2006, vol. 203, pp. 2737-2747.

Fujisawa et al., "MHC-linked susceptibility to type 1 diabetes in the NOD mouse: further localization of Idd16 by subcongenic analysis," Ann. NY Acad. Sci., 2006, vol. 1079, pp. 118-121.

Hattori et al., "The NOD mouse: recessive diabetogenic gene within the major histocompatibility complex," Science, 1986, vol. 231, pp. 733-735.

Homann et al., "An immunologic homunculus for type 1 diabetes," J. Clin. Invest., 2006, vol. 116, pp. 1212-1215.

Hovhannisyan et al., "The role of HLA-DQ8 beta57 polymorphism in the anti-gluten T-cell response in coeliac disease," Nature, 2008, vol. 456, pp. 534-538.

Kanagawa et al., "The role of I-A chain in peptide binding and antigen recognition by T cells," Int Immunol., 1998, vol. 9, pp. 1523-1526.

Kobayashi et al., "Conserved T cell receptor alpha-chain induces insulin autoantibodies," Proc. Natl. Acad. Sci. USA., 2008, vol. 105, pp. 10090-10094.

Levisetti et al., "The insulin-specific T cells of nonobese diabetic mice recognize a weak MHC-binding segment in more than one form," J. Immunol., 2007, vol. 178, pp. 6051-6057.

Levisetti et al., "Weak proinsulin peptide-major histocompatibility complexes are targeted in autoimmnne diabetes in mice," Diabetes, 2008, vol. 57, pp. 1852-1860.

Mareeva et al., "Antibody Specific for the Peptide-Major Histocompatibility Complex," J. Biol. Chem., 2004, vol. 279(43), pp. 44243-44249.

Masteller et al., "Peptide-MHC Class II Dimers as Therapeutics to Modulate Antige-Specific T Cell Responses in Autoimmune Diabetes," J. Immunol., 2003, vol. 171, pp. 5587-5595.

Mordes et al., "Rat Models of Type 1 Diabetes: Genetics, Environment, and Autoimmunity," ILAR Journal, 2004, vol. 45, No. 3, pp. 278-291.

Moriyama et al., "Evidence for a primary islet autoantigen (preproinsulin 1) for insulitis and diabetes in the nonobese diabetic mouse," Proc. Natl Acad. Sci. USA, 2003, vol. 100, pp. 10376-10381.

Nakayama et al., "Prime role for an insulin epitope in the development of type 1 diabetes in NOD mice," Nature, 2005, vol. 435(7039), pp. 220-223, author manuscript, 10 pages.

Nakayama et al., "Priming and effector dependence on insulin B:9-23 peptide in NOD islet autoimmnnity," J. Clin. Invest., 2007, vol. 117, pp. 1835-1843.

Oikonmakos et al., "Allosteric inhibition of glycogen phosphorylase alpha by the Ppotential Aantidiabetic drug 3-isopropyl 4-(2-chorophenyl)-1,4-dihydro-1-ethyl-2-methyl-pyridine-3,5,6-tricarboxylate," Protein Science, 1999, vol. 8, pp. 1930-1945.

Pietropaolo et al., "Primer: Immunity and Autoimmunity," Diabetes, 2008, vol. 57, pp. 2872-2882.

Puri et al., "Modulation of the Immune Response in Multiple Sclerosis," J. Immunol., 1997, vol. 158, pp. 2471-2476.

Sosinowski et al., "Type 1 diabetes: primary antigen/peptide/register/trimolcular complex," Immunol. Res., 2013, vol. 55, pp. 270-276.

Suri et al., "The Murine Diabetogenic Class II Histocompatibility Molecule I-A (g7): Structural and Functional Properties and Specificity of Peptide Selection," Adv. Immunol., 2005, vol. 88, pp. 235-265.

Thomson et al., "FK 506: A novel immunosuppressant for treatment of autoimmune disease: Rationale and preliminary clinical experience," Springer Semin Immunopathol. 1993, vol. 14(4), 31 pages.

Todd et al., "A molecular basis for MHC class II associated autoimmunity," Science, 1988, vol. 240, pp. 1003-1009.

Wallis et al., "Type 1 Diabetes in the BB rat: A polygenic disease," Diabetes, 2009, vol. 58(4), pp. 1007-1017.

Wicker et al., "Type 1 diabetes genes and pathways shared by humans and NOD mice," J. Autoimmun., 2005, vol. 25 (Suppl), pp. 29-33.

Zhang et al., "Immunization with an insulin peptide-MHC complex to prevent type 1 diabetes of NOD mice," Diabetes Meta Res Rev, 2011, vol. 27, pp. 784-789.

Zhong et al., "Production, specificity, and functionality of monoclonal antibodies to specific peptide-major histocompatibility complex class II complexes formed by processing of exogenous protein," Proc. Natl. Acad. Sci. USA, 1997, vol. 94, pp. 13856-13861.

International Search Report and Written Opinion for International Patent Application No. PCT/US10/37495, mailed Oct. 12, 2010, 10 pages.

International Search Report and Written Opinion for International Patent Application No. PCT/US10/37166, mailed Oct. 25, 2010, 12 pages.

Extended European Search Report for European Patent Application No. 10784057.1, dated Mar. 14, 2013, 9 pages.

\* cited by examiner 1,3,6,8-Tetraazatricyclo(4.4.1.1(3,8)) dodecane ($C_8H_{16}N_4$)
CAS#: 51-46-7

8-1.1α1 = T cell responding to insulin B:9-23
4-8 5KC cells = T cell responding to insulin B:9-23
BDC 2.5 = T cell responding to a chromogranin peptide

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 1

Ser Gly Glu Gly Ser Phe Gln Pro Ser Gln Glu Asn Pro
1               5                   10

<210> SEQ ID NO 2
<211> LENGTH: 15
```

```
<212> TYPE: PRT
<213> ORGANISM: Artificial Sequence
<220> FEATURE:
<223> OTHER INFORMATION: Synthetic Peptide

<400> SEQUENCE: 2

Ser His Leu Val Glu Ala Leu Tyr Leu Val Cys Gly Glu Arg Gly
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 3

Glu Lys Ala His Arg Pro Ile Trp Ala Arg Met Asp Ala Lys Lys
1               5                   10                  15
```

COMPOUNDS THAT MODULATE AUTOIMMUNITY AND METHODS OF USING THE SAME

CROSS REFERENCE TO RELATED APPLICATIONS

This application is a national stage application under 35 U.S.C. 371 of PCT Application No. PCT/US2012/039849, having an international filing date of May 29, 2012, which designated the United States, which PCT application claimed the benefit of priority under 35 U.S.C. §119(e) to U.S. Provisional Patent Application Ser. No. 61/490,417, filed May 26, 2011 and U.S. Provisional patent application Ser. No. 61/580,188, filed Dec. 23, 2011, all of which are incorporated herein by reference.

GOVERNMENT INTEREST

This invention was made with government support under grant number DK055969 awarded by the National Institutes of Health. The U.S. government has certain rights in the invention.

TECHNICAL FIELD

The invention relates to therapeutic compounds, pharmaceutical compositions containing the same and their use in the prevention or treatment of autoimmune diseases, such as autoimmune diabetes and celiac disease.

BACKGROUND OF INVENTION

Autoimmune disorders are diseases caused by the body producing an inappropriate immune response against its own tissues, in which the immune system creates T lymphocytes and autoantibodies that attack one's own cells, tissues, and/or organs. Researchers have identified 80-100 different autoimmune diseases and suspect at least 40 additional diseases have an autoimmune basis.

Autoimmune disorders are classified into two types, organ-specific (directed mainly at one organ) and non-organ-specific (widely spread throughout the body). Examples of organ-specific autoimmune disorders are insulin-dependent Type 1 diabetes, which affects the pancreas, Hashimoto's thyroiditis and Graves' disease, which affects the thyroid gland, pernicious anemia, which affects the stomach, Addison's disease, which affects the adrenal glands, chronic active hepatitis, which affects the liver and myasthenia gravis which, affects the muscles. Examples of non-organ-specific autoimmune disorders are rheumatoid arthritis, multiple sclerosis and lupus.

Autoimmune diseases are often chronic, debilitating and life-threatening. The National Institutes of Health (NIH) estimates up to 23.5 million Americans suffer from autoimmune disease and that the prevalence is rising. It has been estimated that autoimmune diseases are among the ten leading causes of death among women in all age groups up to 65 years. Most autoimmune diseases cannot yet be treated directly, but are treated to alleviate the symptoms associated with the condition. Some of the current treatments include administration of corticosteroid drugs, non-steroidal anti-inflammatory drugs (NSAIDs) or more powerful immunosuppressant drugs such as cyclophosphamide, methotrexate and azathioprine that suppress the immune response and stop the progression of the disease. Radiation of the lymph nodes and plasmapheresis (a procedure that removes the diseased cells and harmful molecules from the blood circulation) are other ways of treating an autoimmune disease. However, these treatments often have devastating long-term side effects.

One of the most prevalent organ-specific autoimmune diseases, Type 1 diabetes, is characterized by the production of autoantibodies that target the insulin-secreting pancreatic beta cells. The destruction of the beta cells is mainly due to the action of T cells. In most cases, T cells can respond to an antigen only when the antigen is properly presented by an antigen presenting cell expressing the appropriate major histocompatibility complex (MHC) molecule. Thus, T cell immune response to an antigen requires recognition by the T cell receptor of an antigen coupled to a MHC molecule, and this recognition requires the assembly of a tri-molecular complex between an antigen, a MHC molecule and T cell receptor. In particular, the recognized peptide (when peptide autoantigen) must be in an appropriate register (or position along the MHC peptide binding groove).

Evidence strongly indicates that insulin/proinsulin is a key or primary auto-antigen in the development of type 1 diabetes in the NOD (non-obese diabetic) mouse model. Initial cloning of T cells from islets of NOD mice led to the discovery that the native insulin B chain amino acids 9-23 (B:9-23 insulin peptide) is the dominant antigenic peptide epitope presented by the class II MHC molecule I-A. Mice lacking the native B:9-23 sequence fail to develop diabetes and development of insulin autoantibodies and insulitis are markedly decreased. Restoring the native B:9-23 sequence with an islet transplant (but not bone marrow transplant) or peptide immunization, or a native proinsulin transgene, restores anti-insulin autoimmunity and generates CD4 T cells that cause diabetes.

The major genetic determinant of islet autoimmunity and diabetes in man and animal models are genes within the major histocompatibility complex, and in particular, class II MHC alleles. The NOD mice's unique sequence of IA (homologous to DQ of man) and lack of expression of I-E (shared with many standard mouse strains) are essential for the development of diabetes. The crystal structure of I-A$^{g7}$ with bound peptides has allowed the modeling of peptide binding to this molecule. Similar modeling has been performed for the human diabetogenic allele/molecule DQ8, which has analogous sequence to I-A$^{g7}$. Unanue and coworkers have defined two different registers of binding of the B:9-23 peptide to I-A$^{g7}$ and multiple investigators have utilized the B:9-23 peptide for prevention of diabetes (Levisetti M G, Suri A, Petzold S J, and Unanue E R, J. Immunol. 178(10):6051-6057 (2007); Bresson DL von Herrath M, Autoimmun. Rev. 6(5):315-322 (2007); Fukushima K, Abiru N, Nagayama Y et. al., Biochem. Biophys. Res. Com. 367(4):719-724, 2008).

There are alternative hypotheses as to why I-A$^{g7}$ (and DQB1*0302 44) is associated with islet autoimmunity. One hypothesis is that the molecule is a poor binder of peptides and potentially unstable, and such instability or defective binding might limit negative selection of autoimmune T cells within the thymus. Another hypothesis is that I-A$^{g7}$ is critical for presentation of specific autoantigenic peptide(s) in the periphery. The second hypothesis is supported by the observation that I-A alleles such as IA$^k$ prevent NOD diabetes but enhance alternative autoimmune disorders, suggesting that class II alleles determine the specific organ targeted rather than general susceptibility to autoimmunity.

Thus, there exists a need in the art for safer and more effective methods for treatment and prevention of autoimmune diseases. The instant invention addresses these needs by providing small molecules useful in the treatment and prevention of autoimmune diseases.

SUMMARY OF INVENTION

The present invention is drawn to small molecules (molecular weight less than 500) that can inhibit insulin/proinsulin or gliadin peptides presented by class II MHC molecules and subsequent T cell receptor recognition of these peptide-MHC complexes, as well as therapeutic uses of these molecules to prevent or slow the formation of autoimmune diseases, such as diabetes or celiac disease, in a mammal.

The present invention provides compounds that can inhibit the binding peptides (insulin/proinsulin gliadin peptides) presented by class II MHC molecules (mouse and human), and pharmaceutically acceptable salts thereof. The present invention also provides pharmaceutical compositions containing these compounds. The invention also provides methods of using these compounds and pharmaceutical compositions to prevent or modify the development of autoimmune diseases, including diabetes.

One embodiment of the invention is a method of modifying an autoimmune disease by administering to a mammal in need of such treatment, a therapeutically effective amount of a compound that modifies the T cell response to the targeted antigenic peptide of the autoimmune disease. In a preferred aspect of this embodiment, the compound decreases the T cell receptor response to the antigenic peptide. In a more preferred aspect of this embodiment, the compound decreases the T cell response to the antigenic peptide by inhibiting (or preventing or disrupting) the binding of the antigenic peptide to a MHC class II molecule that presents the antigenic peptide to a T cell receptor. In a particularly preferred aspect of this embodiment, the compound inhibits the binding of an insulin peptide to an MHC class II molecule for presentation to CD4+ T cells, thereby preventing the development of autoimmune diabetes. In another particularly preferred aspect of this embodiment, the compound inhibits the binding of a gliadin peptide to an MHC class II molecule for presentation to CD4+ T cells, thereby preventing the development of celiac disease.

In another aspect of this embodiment, the compound is at least one of the compounds of the invention that include:
1,3,6,8 Tetraazatricyclo(4.4.1.1(3,8))dodecane;
N-(2-chlorophenyl)dicarbonimido/ic diamide/imido;
N-(4-(hydroxy(oxido)amino)phenyl)dicarbonimido/ic diamide/imido;
2,2-dihydroxy-N-(2-(trimethyl-5-azanyl)ethyl)hydrazinecarboximidamide;
2,2-dihydroxy-N'-(4-pyridinylmethylene)hydrazinecarboximidohydrazide;
7-methylhexahydro-2,4(1H,3H)-pteridinedione;
N-(1H-imidazol-1-ylmethyl)-N-methylphenylmethanamine;
N-benzyl-N-(1H-imidazol-1-ylmethyl)-N-methylamine;
N-(2-(dimethylamino)ethyl)-2,2-dihydroxyhydrazinecarboximidamide;
2-(((2,2-dihydroxyhydrazino)(imino)methyl)amino)ethyl acetate;
2-piperazinecarbaldehyde thiosemicarbazone;
1,1-bis(2-chloroethyl)hydrazine;
2,2-dihydroxy-N-(2-((hydroxy(oxido)amino)oxy)ethyl)hydrazinecarboximidamide;
N-(4-chlorophenyl)-2,2-dihydroxyhydrazinecarboximidamide;
1-(2-(15-pyridin-1-yl)ethyl)-15-pyridine;
3-(3-hydroxy-4-oxo-1(4H)-pyridinyl)alanine;
2-((2,5-dichlorophenoxy)methyl)-4,5-dihydro-1H-imidazole;
N'-cyclopentylidene-2,2-dihydroxyhydrazinecarboximidohydrazide;
N-((2,2-dihydroxyhydrazino)(imino)methyl)benzenesulfonamide;
2-amino-4-((amino(imino)methyl)amino)butanoic acid;
N-(3-chloropropyl)-2,2-dihydroxyhydrazinecarboximidamide;
N-(2-aminopentanoyl)valine;
1-(2-(2-pyridinyl)ethyl)azonane;
8-(hydroxy(phenyl)methyl)-9H-purin-6-ol;
(5-(hydroxy(oxido)amino)-2,4-dioxo-3,4-dihydro-1(2H)-pyrimidinyl) acetaldehyde semicarbazone;
N-(2-cyanoethyl)-2,2-dihydroxyhydrazinecarboximidamide;
2,2-dihydroxy-N'-(1-methylethylidene)hydrazinecarboximidohydrazide;
2,2-dihydroxy-N-(2-(methylsulfonyl)ethyl)hydrazinecarboximidamide;
N-(2-bromoethyl)-2,2-dihydroxyhydrazinecarboximidamide;
N-benzyl-2,2-dihydroxyhydrazinecarboximidamide;
((3,4-diamino-4-oxobutyl)thio)acetic acid;
2-amino-1-phenyl-1-butanol;
2,2-dihydroxy-N-(2-methoxyethyl)hydrazinecarboximidamide;
3,4-dimethyl-5-phenyl-1,3-oxazolidine;
1-benzyl-3,4-pyrrolidinediol;
2,6-diaminoheptanedioic acid;
N-butyl-N-methyl-1,3,5-triazatricyclo[3.3.1.1(3,7)]decan-7-amine;
1-(2-oxiranylmethyl)-15,3,5,7-tetraazatricyclo[3.3.1.1(3,7)]decane;
1-(3-chloro-2-propenyl)-15,3,5,7-tetraazatricyclo[3.3.1.1(3,7)]decane;
142,3-dibromo-2-propenyl)-15,3,5,7-tetraazatricyclo[3.3.1.1(3,7)]decane;
2,3,6,7,10,11-hexahydrotriimidazo[1,2-a:1,2-c:1,2-e][1,3,5] triazine;
1-benzyl-15,3,5,7-tetraazatricyclo[3.3.1.1(3,7)]decane;
1-(2-chloro-2-propenyl)-15,3,5,7-tetraazatricyclo[3.3.1.1(3,7)]decane;
tetradecahydro-2,3-phenazinediamine;
1-(4-chloro-2-butenyl)-15,3,5,7-tetraazatricyclo[3.3.1.1(3,7)]decane;
2-amino-N-(3-(dichloromethyl)-5,6,8-trihydroxy-3-methyl-1-oxo-3,4,4a,5,6,7-hexahydro-1H-isochromen-4-yl)propanamide;
2-(15,3,5,7-tetraazatricyclo[3.3.1.1(3,7)]dec-1-yl)ethanol;
1-bromo-15,3,5,7-tetraazatricyclo[3.3.1.1(3,7)]decane;
1-(2-(1,3-benzodioxol-5-yl)-1-methylethyl)hydrazine;
1-(2,4,5-trichlorobenzyl)-15,3,5,7-tetraazatricyclo[3.3.1.1(3,7)]decane;
1-(15,3,5,7-tetraazatricyclo[3.3.1.1(3,7)]dec-1-yl)acetone;
1-allyl-15,3,5,7-tetraazatricyclo[3.3.1.1(3,7)]decane;
5,6-diamino-1,3-dimethyldihydro-2,4(1H,3H)-pyrimidinedione;
hydroxy(phenyl)methylphosphinic acid;
1,2-dichloro-N1,N1,N1,N1,N2,N2,N2,N2-octamethyl-1,1,2,2-ethanetetramine;
3-(aminomethyl)-2,4,5,6-tetrachlorobenzylamine;
2-(methylthio)-4,6-bis(trimethyl-5-azanyl)pyrimidine;
ethyl 15,4-diazabicyclo[2.2.2]oct-1-ylcarbamate;
2,2'-disulfanediylbis(3-aminopropanoic acid;
methyl 4,4-dichloro-2-(1-piperazinyl)-3-butenoate;

N-(aminoacetyl)-4-hydroxyphenylalanine;
1-ethyl-15,3,5,7-tetraazatricyclo[3.3.1.1(3,7)]decane;
1,4,7-triazacyclotridecane;
5,5'-bis(hydroxymethyl)-3,3',5,5'-tetramethyl-3,3'-bimorpholine-2,2'-dione;
S-((2-amino-2-azetidinyl)methyl)hydrogen thiosulfate;
4,4'-(cyclohexane-1,2-diyl)dipiperazine-2,6-dione;
2-methylene-3-phenyl-1-azabicyclo[2.2.2]oct-3-yl propionate;
(E)-4,4'-(ethene-1,2-diyl)dibenzimidamide;
1-acetyl-3',4',5',6'-tetrahydro-1'H-spiro[indoline-3,2'-pyrimidin]-2-one;
3-phenoxyproline;
1'-acetyl-4-methylspiro[imidazolidine-2,3'-indolin]-2'-one;
1,3,6,8-Tetraazatricyclo (6.2.1.1(3,6))dodecane;
S-(2-(dimethylamino)ethyl)hydrogen thiosulfate;
8-Azaguanine;
[1,3]dithiolo[4,5-b]quinoxaline-2,2-diamine;
9-thia-1,3,6,8 tetraazatricyclo[4.3.1.1~3,8~]undecane 9,9-dioxide;
4,5-dihydroxy-3-nitroso-2,7-naphthalenedisulfonic acid;
(2,4-diiodophenoxy)acetic acid;
5-bromo-3-cyclohexyl-2-hydroxybenzamide;
5-chloro-2-(2-methoxy-2-oxoethoxy) benzoic acid;
5-((2,5-dichloro-4-(hydroxy(oxido)amino)phenyl)diazenyl)-2-imino-4-methyl-2,3-dihydro-1,3-thiazole;
7-methoxy-10H-pyrido[2,3-b]pyrimido[4,5-e][1,4]thiazine-2,4-diamine;
2-amino-4-hydroxy-6-mercapto-7-pteridine carboxylic acid;
3-(carboxymethoxy)-6-oxo-3,6-dihydro-1(2H)-pyridazinyl) acetic acid;
2-(1H-tetraazol-5-yl)ethanesulfonic acid;
3-phosphonopropylphosphonic acid;
1,3-dihydroxy-1,3-propanedisulfonic acid;
3-deoxy-2,4-dithiopentaric acid;
3-ethylidene-1,2-cyclopropanedicarboxylic acid; and,
pharmaceutically-acceptable salts thereof.

In a specific embodiment, the compound is at least one of the compounds of the invention selected from:
1,3,6,8-tetraazatricyclo[4.4.1.1(3,8)]dodecane,
1-ethyl-15,3,5,7-tetraazatricyclo[3.3.1.1(3,7)]decane,
1-allyl-15,3,5,7-tetraazatricyclo[3.3.1.1(3,7)]decane,
1-(15,3,5,7-tetraazatricyclo[3.3.1.1(3,7)]dec-1-yl)acetone,
1-(2,4,5-trichlorobenzyl)-15,3,5,7-tetraazatricyclo[3.3.1.1(3,7)]decane,
1-bromo-15,3,5,7-tetraazatricyclo[3.3.1.1(3,7)]decane,
2-(15,3,5,7-tetraazatricyclo[3.3.1.1(3,7)]dec-1-yl)ethanol,
1-(4-chloro-2-butenyl)-15,3,5,7-tetraazatricyclo[3.3.1.1(3,7)]decane,
1-(2-chloro-2-propenyl)-15,3,5,7-tetraazatricyclo[3.3.1.1(3,7)]decane,
1-benzyl-15,3,5,7-tetraazatricyclo[3.3.1.1(3,7)]decane,
1-(2,3-dibromo-2-propenyl)-15,3,5,7-tetraazatricyclo[3.3.1.1(3,7)]decane,
1-(3-chloro-2-propenyl)-15,3,5,7-tetraazatricyclo[3.3.1.1(3,7)]decane,
1-(2-oxiranylmethyl)-15,3,5,7-tetraazatricyclo[3.3.1.1(3,7)]decane, and
pharmaceutically-acceptable salts thereof.

In another embodiment, the invention is a method of preventing the formation of diabetes in a mammal by administering to the mammal a compound that inhibits the T cell response to an insulin peptide presented by an MHC class II molecule. In another aspect of this embodiment, the insulin peptide is B:9-23, the MHC class II molecule is DQ8 and the T cell displays a CD4$^+$ TCR. In one aspect of this embodiment, the compound is administered to the mammal in a pharmaceutical composition of the invention.

In another embodiment, the invention is a method of preventing the formation of celiac disease in a mammal by administering to the mammal a compound that inhibits the T cell response to a gliadin peptide presented by an MHC class II molecule. In another aspect of this embodiment, the gliadin peptide has the sequence 228-SGEGSFQPSQENP-240 (SEQ ID NO:1), the MHC class II molecule is DQ8 and the T cell displays a CD4$^+$ TCR. In one aspect of this embodiment, the compound is administered to the mammal in a pharmaceutical composition of the invention.

One embodiment of this invention is a method of preventing or treating autoimmune diseases, or ameliorating the symptoms of these diseases, by administering a therapeutically effective amount of one of these compounds, or a pharmaceutically acceptable salt thereof, to a mammal in need of such treatment or suspected of having an autoimmune disease or having a propensity to develop an autoimmune disease. In preferred embodiments, the autoimmune disease is autoimmune (Type 1) diabetes or celiac disease.

Another embodiment of this invention is a method of treating an autoimmune disease such as Type 1 diabetes or celiac disease, or ameliorating a symptom thereof, by administering a therapeutically effective combination of at least one of the compounds of the present invention and one or more other known anti-diabetic or anti-inflammatory or anti-celiac disease compounds. For example, other anti-diabetic compounds may include at least one of an alpha-glucosidase inhibitor, a biguanide, a Dpp-4 inhibitor, a meglitinide, a sulfonylurea, a thiazolidinedione or combinations thereof.

Another embodiment of the present invention is a method of modulating the activity of a T cell hybridoma by contacting the cells with at least one compound of the present invention in the presence of class II MHC molecules bound to an insulin or glaidin protein or to a peptide fragment thereof. Preferably, the MHC class II molecule is DQ8, or a homologous protein, bound to the B:9-23 insulin peptide or a gliadin peptide.

Another embodiment of the present invention is a method of disrupting or otherwise decreasing the binding of a MHC class II molecule bound to an insulin or gliadin protein or to a peptide fragment thereof by contacting the MHC class II molecule with a compound of the present invention in the presence of an insulin or gliadin protein or to a peptide fragment thereof.

Another embodiment of this invention is a method of testing the susceptibility of a mammal to treatment with one of the compounds of the present invention by testing the mammal for the presence of antibodies to a MHC class II molecule bound to an insulin or gliadin protein or to a peptide fragment thereof, wherein the presence of antibodies that recognize the MHC class II molecules is indicative of the presence or likely development of an autoimmune disease, such as diabetes or celiac disease. In a further embodiment, a mammal found to have antibodies to a MHC class II molecule bound to an insulin or gliadin protein or to a peptide fragment thereof is selected for treatment for diabetes or celiac disease. In a related embodiment, the treatment provided to the mammal selected for treatment includes the administration of at least one therapeutic composition of the present invention.

Additionally, the invention provides pharmaceutical compositions containing one or more compounds of the present invention with at least one pharmaceutically acceptable carrier.

Also provided herein are pharmaceutical packages comprising a pharmaceutical composition comprising therapeutically-effective amounts of at least one therapeutic compound of the invention, optionally together with at least one pharmaceutically acceptable carrier. The pharmaceutical compositions may be administered separately, simultaneously or sequentially, with other compounds or therapies used in the prevention, treatment or amelioration of an autoimmune disease such as diabetes or celiac disease.

Also provided herein are pharmaceutical kits containing a pharmaceutical composition of at least one compound of the invention, optionally together with at least one pharmaceutically acceptable carrier; prescribing information and a container. The prescribing information may describe the administration, and/or use of these pharmaceutical compositions alone or in combination with other therapies used in the prevention, treatment or amelioration of an autoimmune disease such as diabetes or celiac disease.

Also provided herein are methods for the prevention, treatment or prophylaxis of diabetes or celiac disease in a mammal comprising administering to a mammal in need thereof therapeutically effective amounts of any of these pharmaceutical compositions of the invention.

Also provided herein are methods for delaying the onset of diabetes or celiac disease in a mammal comprising administering to the mammal therapeutically effective amounts of at least one compound of the invention, including, for example, the pharmaceutical compositions comprising at least one compound of the invention.

In one aspect, the invention provides for the use of a compound of the invention in the manufacture of a medicament for the treatment of an autoimmune disease and particularly (Type 1) diabetes or celiac disease.

In another aspect, the invention provides the use of a compound or composition of the invention for use in the treatment of an autoimmune disease and particularly (Type 1) diabetes or celiac disease.

In another aspect, the invention provides for the dietary management of an autoimmune disease, and particularly (Type 1) diabetes or celiac disease, in an individual comprising administering an effective amount of the compounds or compositions of the invention to the individual in need thereof.

In another aspect, the invention provides for the clinical dietary management of an autoimmune disease, and particularly (Type 1) diabetes or celiac disease, in an individual comprising administering an effective amount of the compounds or compositions of the invention to the individual in need thereof.

In another aspect, the invention provides for the clinical dietary management of metabolic processes associated with an autoimmune disease, and particularly (Type 1) diabetes or celiac disease, a cardiovascular disorder or disease, or condition associated with cardiovascular disease in an individual comprising administering an effective amount of compounds or compositions of the invention to the individual in need thereof.

In another aspect, the invention provides methods of preventing an autoimmune disease, and particularly (Type 1) diabetes or celiac disease, comprising administering an effective amount of a compound or composition of the invention to an individual in need of such pretreatment.

Other aspects of the invention will be set forth in the accompanying description of embodiments, which follows and will be apparent from the description or may be learnt by the practice of the invention. However, it should be understood that the following description of embodiments is given by way of illustration only since various changes and modifications within the spirit and scope of the invention will become apparent to those skilled in the art and are encompassed within the scope of this invention.

BRIEF DESCRIPTION OF DRAWINGS

FIG. 1A shows the results of the T cell stimulation assay with anti-B:9-23 T cell hybridomas in culture with insulin B:9-23 peptide and small molecules for pocket 4, and FIG. 1B shows the results of the T cell stimulation assay with anti-B:9-23 T cell hybridomas in culture with insulin B:9-23 peptide and small molecules for pocket 6. "p9:14" refers to "pocket 9:compound No. 14," which was used as a control compound that does not change stimulation to the B:9-23 peptide.

FIGS. 2A-2F show the inhibition curves for the small molecule inhibitors used in B:9-23 activation of T cells.

FIG. 4 shows the testing of small molecules for their ability to block T cell stimulation from endogenously processed insulin.

228-SGEGSFQPSQENP-240 (SEQ ID NO:1) at 1 µM concentration.

Figure 9A:
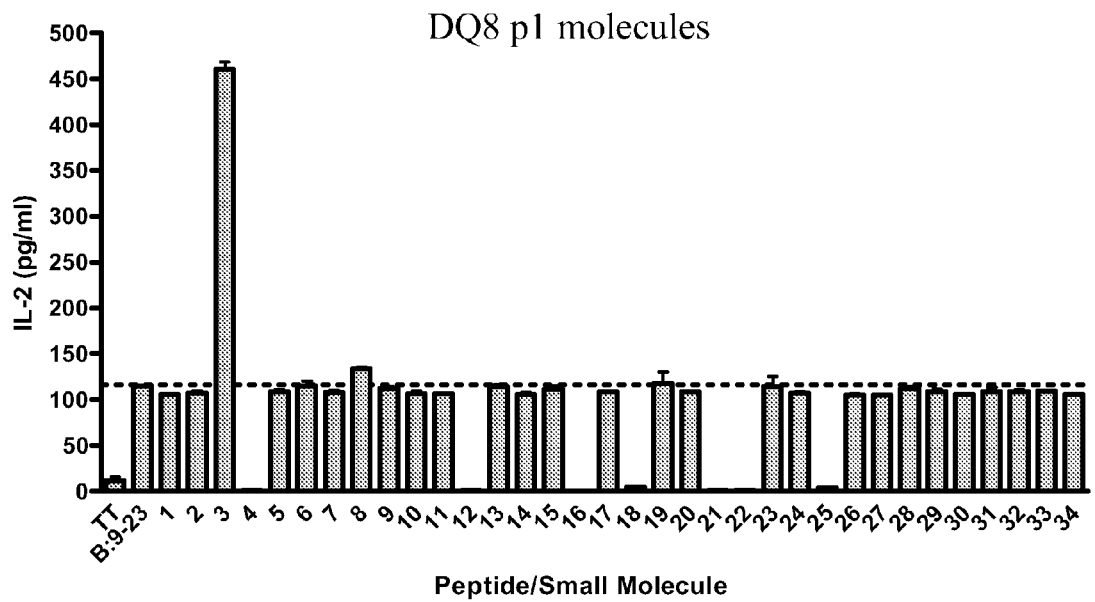
Figure 9B:
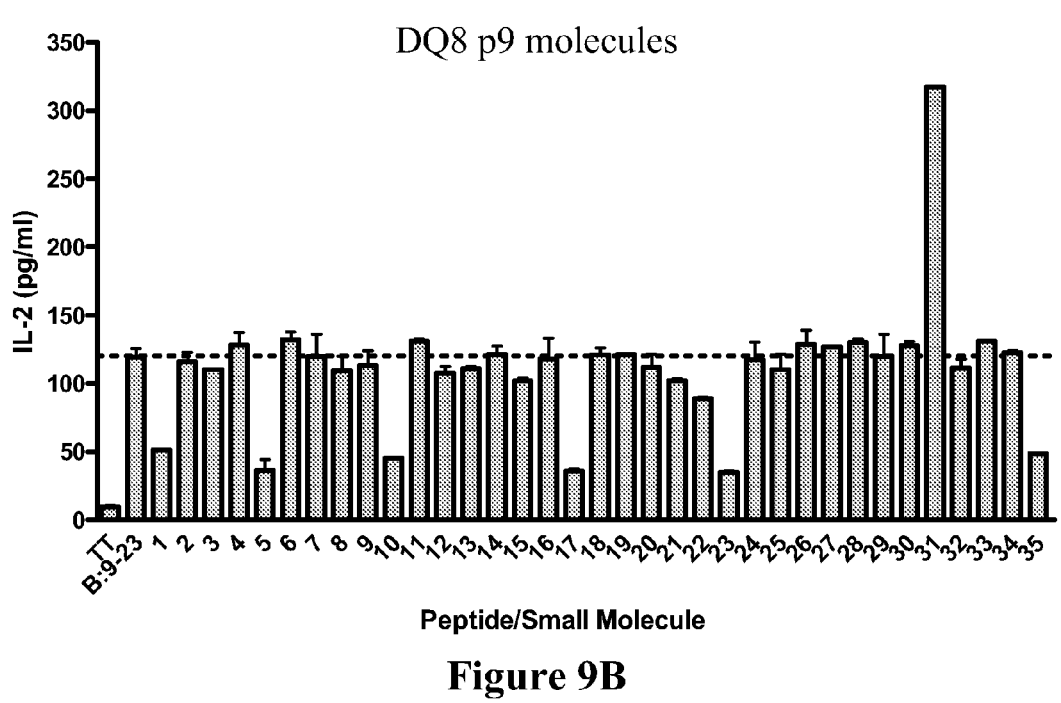

FIGS. 9A and 9B represent the results of the T cell stimulation assay for compounds occupying pocket 1 and pocket 9 of the human DQ8 peptide binding groove, respectively.

Figure 10A:
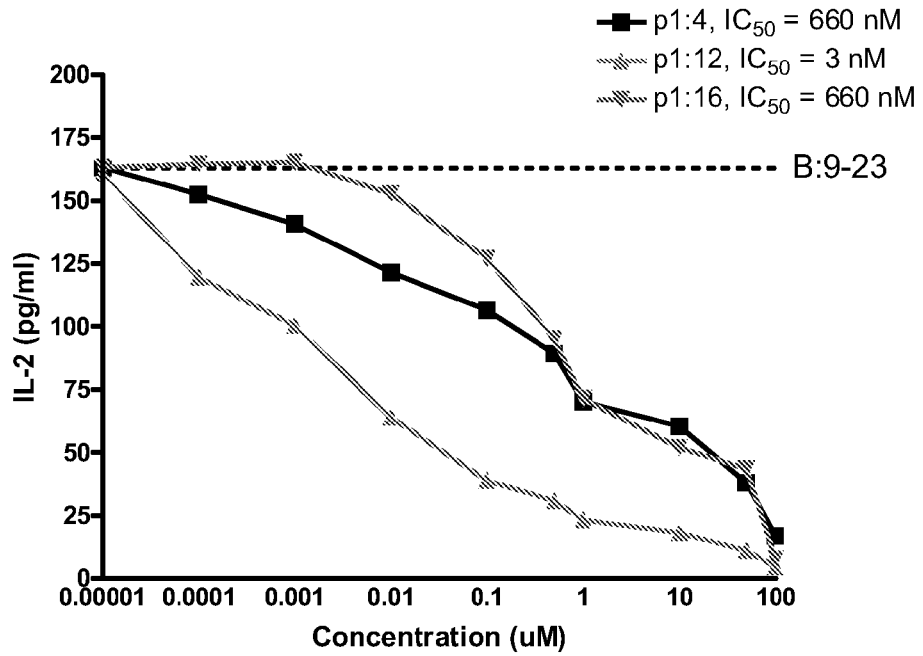

FIG. 10A shows the inhibition of a human T cell receptor recognizing insulin B:9-23 presented by human DQ8 by certain pocket 1 binding small molecules identified in FIG.

Figure 10B:
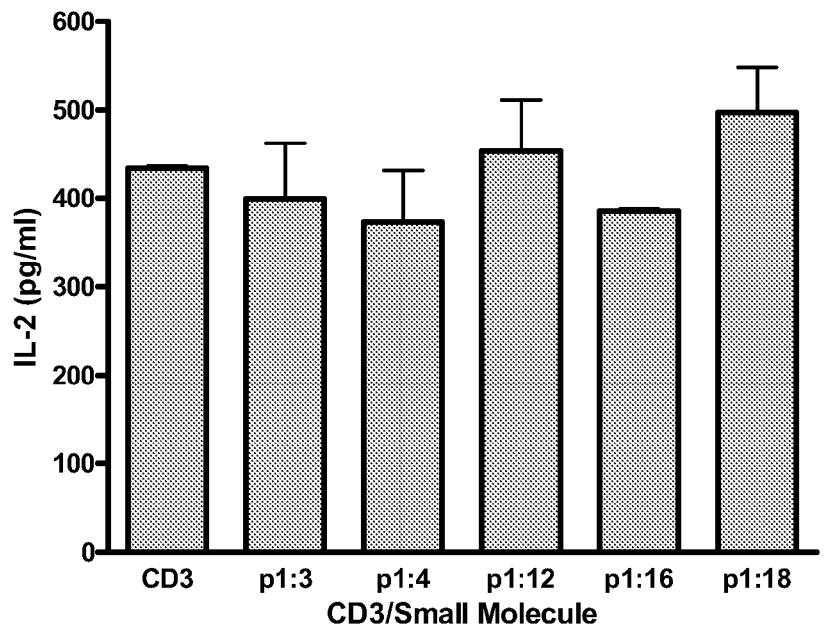

9A. FIG. 10B shows that these pocket 1 binding molecules did not change response to CD3-stimulated T cell hybridomas.

Figure 11:
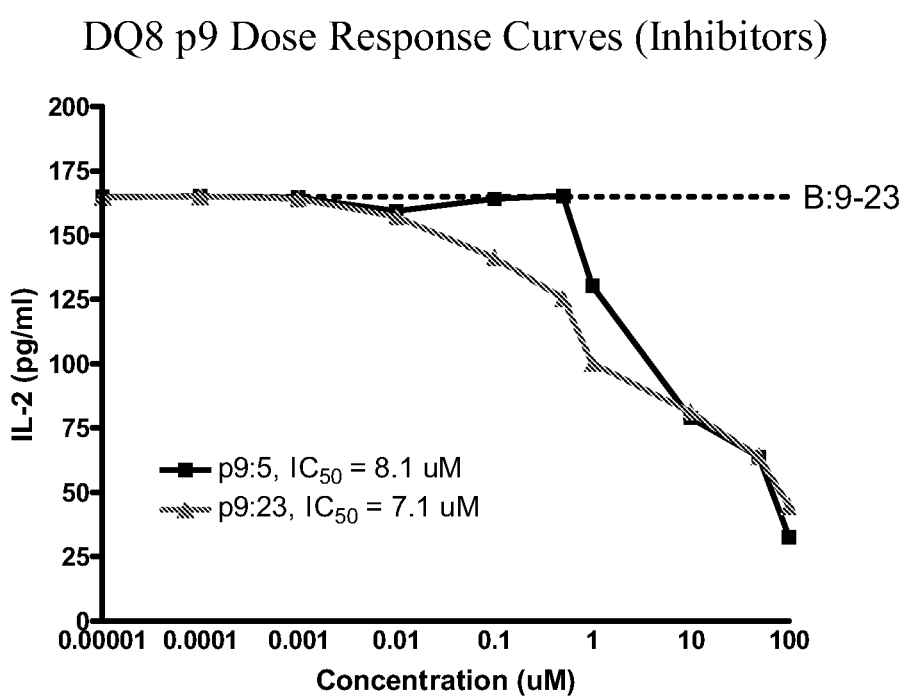

FIG. 11 shows the inhibition of a human T cell receptor recognizing insulin B:9-23 presented by human DQ8 by certain pocket 9 binding small molecules identified in FIG. 9B.

Figure 12:
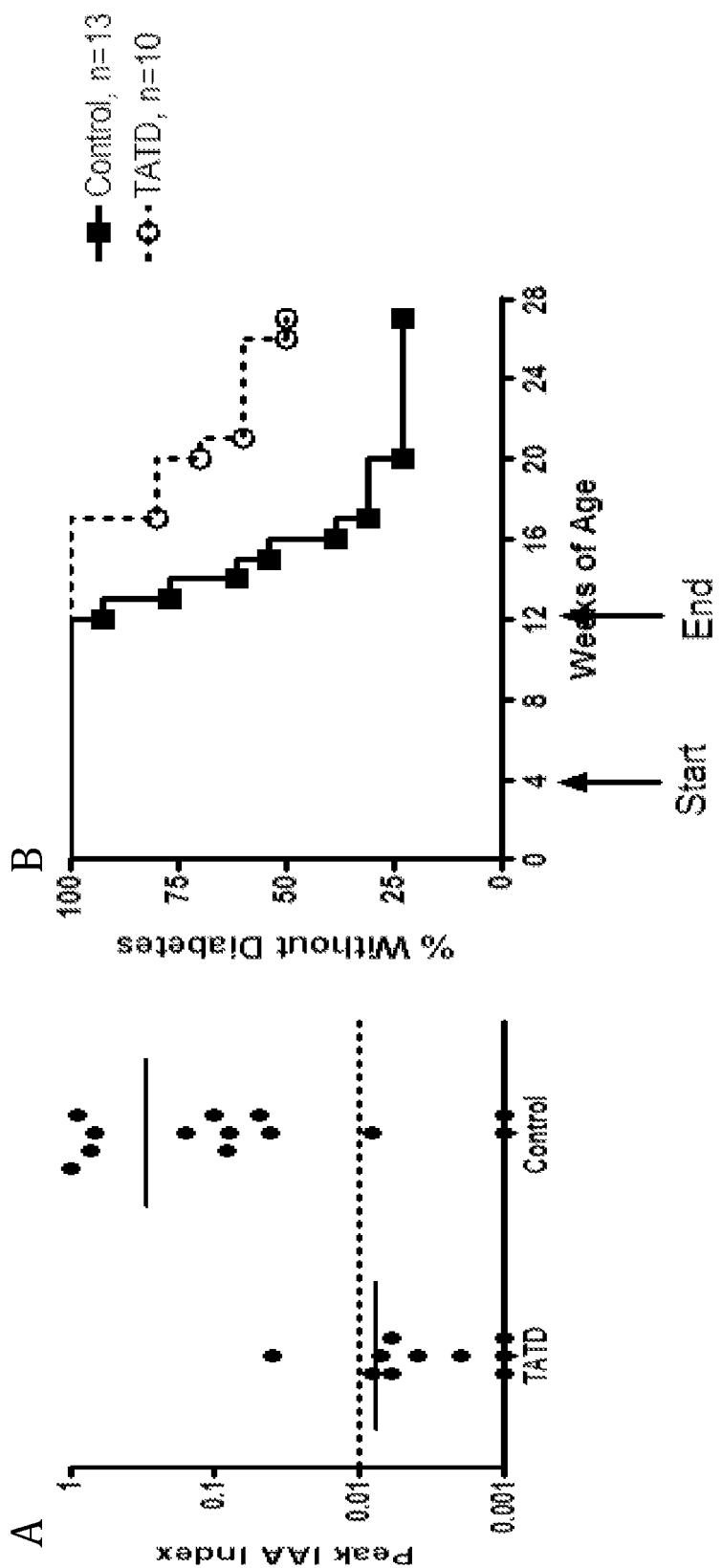

FIG. 12 shows an in vivo preclinical therapeutic evaluation of a putative pocket 6 binding agent, TATD. FIG. 12A shows peak insulin autoantibody (IAA) titers in NOD mice, up to 24 weeks of age. FIG. 12B shows a life table of diabetes incidence of treated and control NOD mice.

Figure 13:
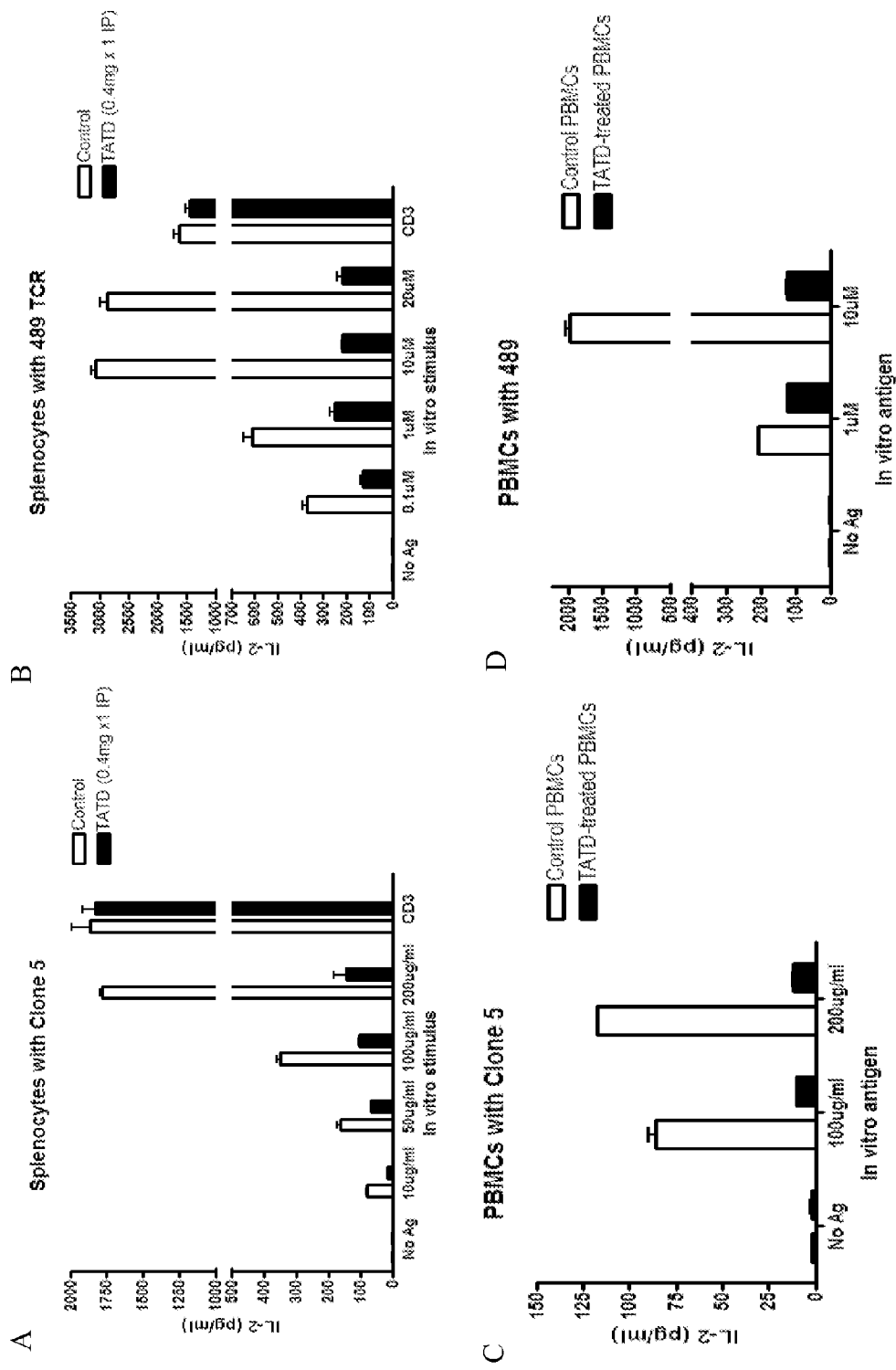

FIG. 13 shows the results of the ex vivo biomarker assay to monitor the in vivo effect of TATD on antigen presentation. The IL-2 response from the TCR transfectomas using splenocytes harvested within 2 hours from TATD treated mice was abrogated compared to PBS treated controls (FIGS. 13A and 13B). Pooled PBMCs from TATD treated mice showed similar effects on IL-2 production inhibiting both TCR transfectomas (FIGS. 13C and 13D).

DETAILED DESCRIPTION OF THE INVENTION

The present invention describes novel compositions and methods for the prevention or treatment of an autoimmune disease. Recognition of an autoantigenic peptide is dependent upon presentation of the auto-antigenic peptide by a MHC molecule present on an antigen presenting cell (APC) to a specific T cell receptor (TCR). Assembly of a trimolecular complex comprising the auto-antigenic peptide, the MHC molecule and the TCR is required to trigger the T cell autoimmune response. Described herein is a novel strategy to prevent or disrupt the assembly of the trimolecular complex and thus prevent the triggering of the auto immune response. The strategy is based on identification of small molecules (having molecular weight less than 500) that are capable of binding the MHC class II molecule presumably interfering with the binding of the autoantigenic peptide with the MHC molecule, thus preventing the recognition of the autoantigenic peptide by the TCR and inhibiting the TCR autoimmune response.

Figure 2A:
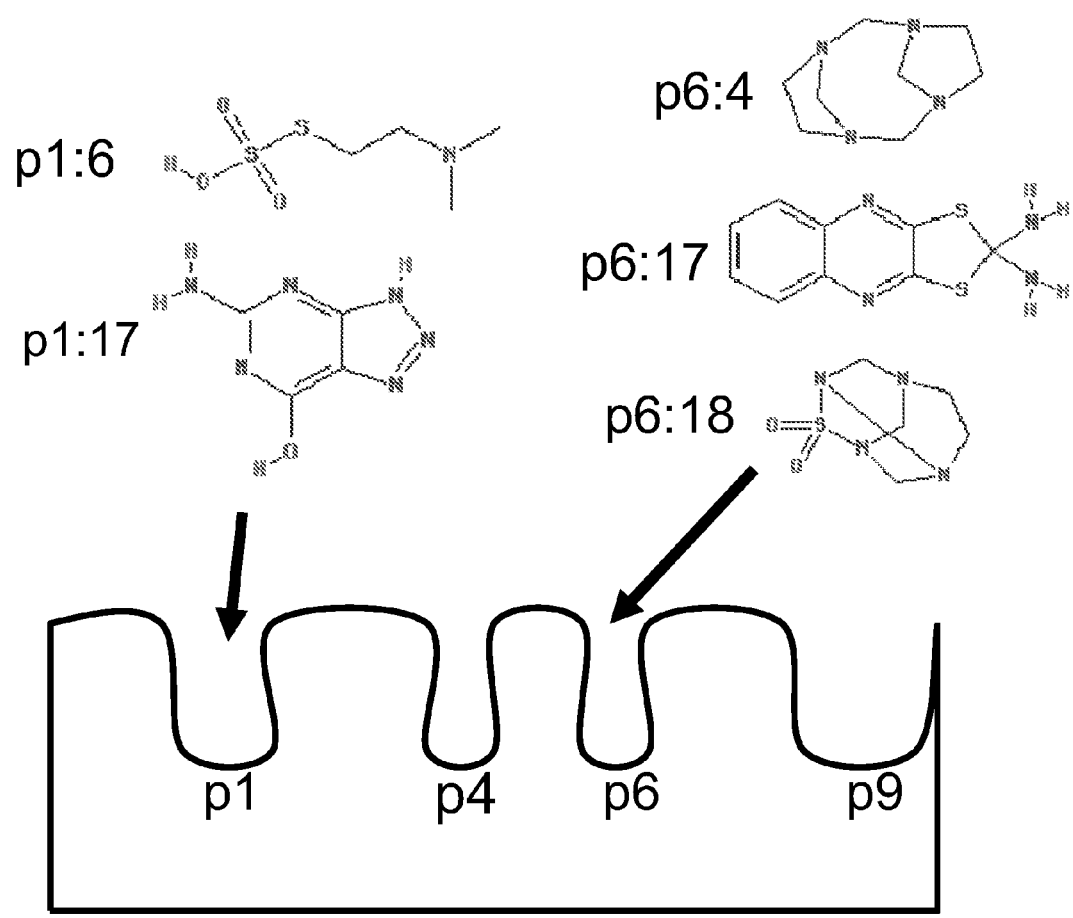
FIG. 2A shows the diagram of the structural pockets (pocket 1:p1, pocket 4:p4, pocket 6:p6, and pocket 9:p9) along the I-A$^{g7}$ binding groove with the proposed binding sites for exemplary compound structures based upon in silico molecular modeling.
Figure 2B:
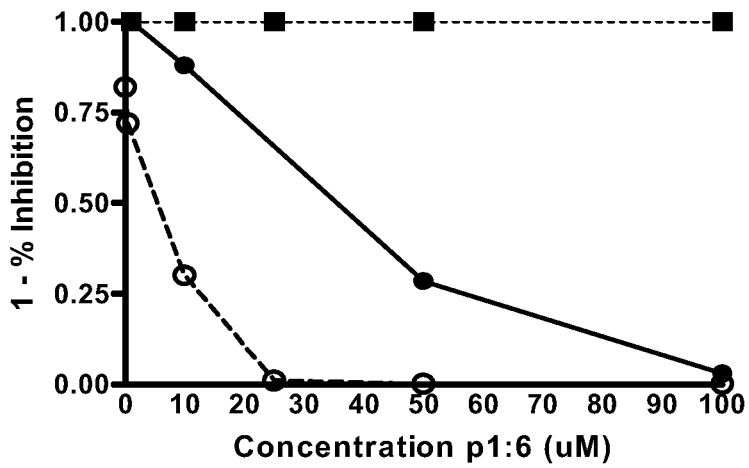
Figure 2C:
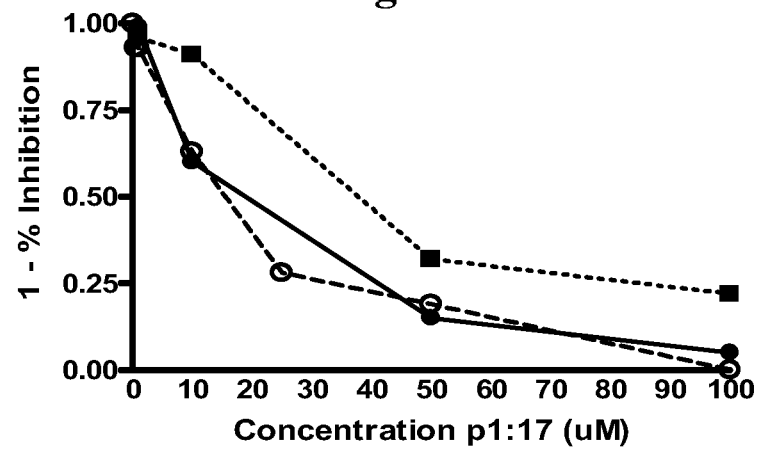
Figure 2D:
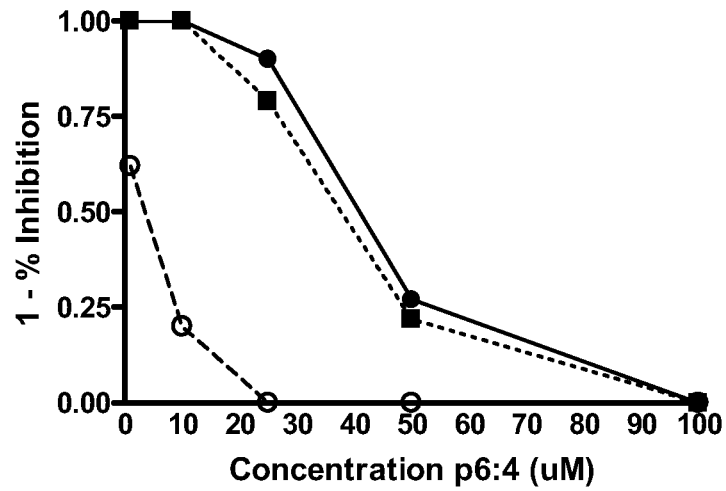
Figure 2E:
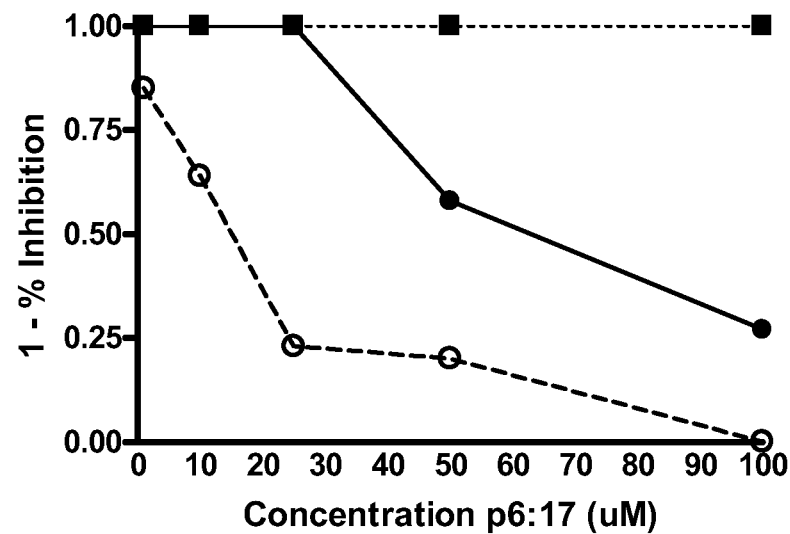
Figure 2F:
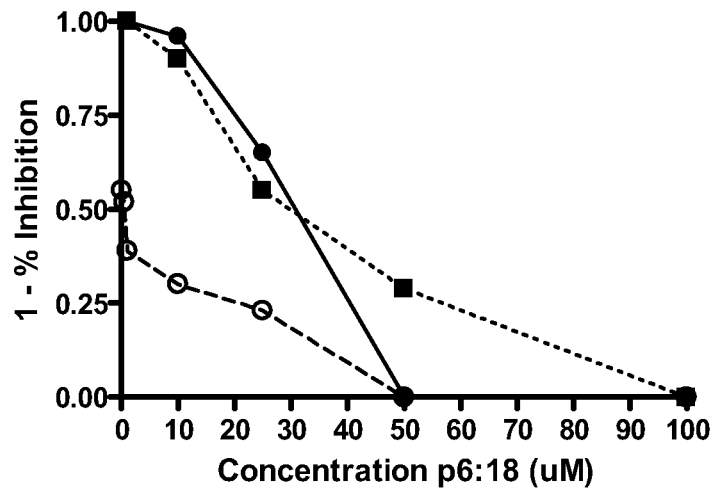

Distinct structural pockets (designated herein as p1, p4, p6, and p9) that accommodate peptide side chains exist along the peptide binding groove of the class II MHC molecules I-A$^{g7}$ (mouse) and HLA-DQ8 (human) (see FIG. 2A). The I-A$^{g7}$ and DQ8 MHC molecules are implicated in autoimmune diseases, such as, diabetes and celiac disease. The present inventors have utilized in silico molecular docking to screen the National Cancer Institute's (NCI) 140,000 "drug-like" compound library for small molecules capable of binding to pockets 1, 4, 6 and 9 of the I-A$^{g7}$ binding groove, as well as pockets 1 and 9 of the human HLA-DQ8 binding groove. The candidate molecules were tested for their ability to inhibit T cell receptor (TCR) responses. As explained in details in the Examples, this led to identification of molecules that inhibited the B:9-23 peptide, endogenous insulin, and islet stimulated T cell responses. Compounds that would inhibit binding of the B:9-23 insulin peptide to DQ8 are useful in preventing or treating diabetes. Further, as explained in Example 5 these molecules also inhibited the 489 TCR response to alpha gliadin peptides and downregulate IL-2 production. The 489 TCR recognizes alpha-gliadin peptides presented by DQ8 and is involved in celiac disease. Therefore, the small molecules of the present invention are also useful in preventing or treating celiac disease (gluten sensitivity).

Thus, the present invention is drawn to methods of preventing or treating autoimmune diseases such as diabetes and celiac disease by modulating the binding of MHC class II molecules to antigenic peptides or fragments of antigenic peptides of the autoimmune disease by the administration of compounds of the invention, or pharmaceutically-acceptable salts, thereof to a mammal.

The term "insulin peptide" is used to denote a peptide fragment of an insulin protein. Although the fragment is typically a subset of the amino acid sequence of the insulin protein, an insulin peptide may contain the entire amino acid sequence of a naturally-occurring insulin protein.

The term "alpha-gliadin peptide" is used to denote is used to denote a peptide fragment of an alpha-gliadin protein. Although the fragment is typically a subset of the amino acid sequence of the alpha-gliadin protein, an alpha-gliadin peptide may contain the entire amino acid sequence of a naturally-occurring alpha-gliadin protein.

"Modulate" means to alter the ability of an antigenic peptide to associate with an MHC protein molecule, for example, an insulin peptide implicated in autoimmune diabetes (or gliadin peptide implicated in autoimmune celiac disease) to associate with a MHC class II protein molecule. Thus, modulation includes enhancement of the association between an insulin peptide (or gliadin peptide) and a MHC class II protein molecule, as well as dissociation of a bound complex formed by the association of an insulin peptide (or gliadin peptide) bound to a MHC class II protein molecule as well as preventing the formation of a complex between an insulin peptide (or gliadin peptide) and a MHC class II protein molecule.

As used herein, the term "agent" means a chemical or biological molecule such as a simple or complex organic molecule, a peptide, a protein or an oligonucleotide.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically-acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in at page 1418 of Remington's Pharmaceutical Sciences, 17th ed., Mack Publishing Company, Easton, Pa., 1985.

The term "therapeutically-effective amount" of a compound of this invention means an amount effective to modulate the formation or progression of an autoimmune disorder in a host.

It will be appreciated by those skilled in the art that compounds of the invention having a chiral center may exist in, and may be isolated in, optically active and racemic forms. It is to be understood that the compounds of the present invention encompasses any racemic, optically-active, regioisomeric or stereoisomeric form, or mixtures thereof, which possess the therapeutically useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers, which may be formed. For example, if the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically-pure moiety resulting in forms that are separable by fractional crystallization, distillation or chromatography.

The compounds used in making the pharmaceutical compositions of the present invention may be purchased commercially. The compounds of the present invention, including the salts of these compounds, may also be prepared in ways well known to one skilled in the art of organic synthesis. These compounds of this invention may be prepared using the reactions performed in solvents appropriate to the reagents and materials employed and suitable for the transformation being effected. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

Also provided herein are pharmaceutical compositions containing compounds of the invention and a pharmaceutically-acceptable carrier, which are generally accepted in the art for the delivery of biologically active agents to animals, in particular, mammals. Pharmaceutically-acceptable carriers are formulated according to a number of factors well within the purview of those of ordinary skill in the art to determine and accommodate. These include, without limitation: the type and nature of the active agent being formulated; the subject to which the agent-containing composition is to be administered; the intended route of administration of the composition; and, the therapeutic indication being targeted. Pharmaceutically-acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically-acceptable carriers, and factors involved in their selection, are found in a variety of readily available sources, such as Remington's Pharmaceutical Sciences, 17th ed., Mack Publishing Company, Easton, Pa., 1985.

This invention further provides a method of treating a mammal afflicted with an autoimmune disorder or preventing a mammal from developing autoimmunity, which includes administering to the mammal a pharmaceutical composition provided herein. Such compositions generally comprise a therapeutically effective amount of a compound provided herein, that is, an amount effective to prevent, ameliorate, lessen or inhibit an autoimmune disease. Such amounts typically comprise from about 0.1 to about 1000 mg of the compound per kilogram of body weight of the mammal to which the composition is administered. Therapeutically effective amounts can be administered according to any dosing regimen satisfactory to those of ordinary skill in the art.

Administration may be, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffering agents. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

A preferred formulation of the invention is a mono-phasic pharmaceutical composition suitable for parenteral or oral administration for the prevention, treatment or prophylaxis of an autoimmune disease such as diabetes, consisting essentially of a therapeutically-effective amount of a compound of the invention, and a pharmaceutically acceptable carrier.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the therapeutic compounds of the present invention.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The dosage formulations provided by this invention may contain the therapeutic compounds of the invention, either alone or in combination with other therapeutically active ingredients, and pharmaceutically acceptable inert excipients. The term "pharmaceutically acceptable inert excipients" includes at least one of diluents, binders, lubricants/glidants, coloring agents and release modifying polymers.

Suitable antioxidants may be selected from amongst one or more pharmaceutically acceptable antioxidants known in the art. Examples of pharmaceutically acceptable antioxidants include butylated hydroxyanisole (BHA), sodium ascorbate, butylated hydroxytoluene (BHT), sodium sulfite, citric acid, malic acid and ascorbic acid. The antioxidants may be present in the dosage formulations of the present invention at a concentration between about 0.001% to about 5%, by weight, of the dosage formulation.

Suitable chelating agents may be selected from amongst one or more chelating agents known in the art. Examples of suitable chelating agents include disodium edetate (EDTA), edetic acid, citric acid and combinations thereof. The chelating agents may be present in a concentration between about 0.001% and about 5%, by weight, of the dosage formulation.

The dosage form may include one or more diluents such as lactose, sugar, cornstarch, modified cornstarch, mannitol, sorbitol, and/or cellulose derivatives such as wood cellulose and microcrystalline cellulose, typically in an amount within the range of from about 20% to about 80%, by weight.

The dosage form may include one or more binders in an amount of up to about 60% w/w. Examples of suitable binders include methyl cellulose, hydroxypropyl cellulose, hydroxypropylmethyl cellulose, polyvinyl pyrrolidone, eudragits, ethyl cellulose, gelatin, gum arabic, polyvinyl alcohol, pullulan, carbomer, pregelatinized starch, agar, tragacanth, sodium alginate, microcrystalline cellulose and the like.

Examples of suitable disintegrants include sodium starch glycolate, croscarmellose sodium, crospovidone, low substituted hydroxypropyl cellulose, and the like. The concentration may vary from 0.1% to 15%, by weight, of the dosage form.

Examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like. The concentration may vary from 0.1% to 15%, by weight, of the dosage form.

Release modifying polymers may be used to form extended release formulations containing the therapeutic compounds of the invention. The release modifying polymers may be either water-soluble polymers, or water insoluble polymers. Examples of water-soluble polymers include polyvinylpyrrolidone, hydroxy propylcellulose, hydroxypropyl methylcellulose, vinyl acetate copolymers, polyethylene oxide, polysaccharides (such as alginate, xanthan gum, etc.), methylcellulose and mixtures thereof. Examples of water-insoluble polymers include acrylates such as methacrylates, acrylic acid copolymers; cellulose derivatives such as ethylcellulose or cellulose acetate; polyethylene, and high molecular weight polyvinyl alcohols.

Also encompassed by the present invention are methods for screening potential therapeutic agents that modulate the interaction between class II MHC molecules and insulin (or gliadin) peptides comprising the steps of: (a) combining an MHC protein molecule and an insulin (or gliadin) peptide under conditions in which they interact, in the presence of a potential therapeutic agent, and; (b) monitoring the interaction of the MHC molecule and the peptide; wherein a potential therapeutic agent is selected for further study when it modifies the interaction compared to a control sample to which no potential therapeutic agent has been added.

In one embodiment, the potential therapeutic agent is selected from the group consisting of a pharmaceutical agent, a cytokine, a small molecule drug, a cell-permeable small molecule drug, a hormone, a combination of interleukins, a lectin, a bispecific antibody, a peptide mimetic, and a sense or antisense oligonucleotide.

In another embodiment, the MHC molecule is a class II MHC molecule. In a preferred embodiment, the class II MHC molecule is DQ8 that has a similar pocket 4 or 6 binding region and is associated with diabetes risk in man, or a fragment of DQ8 sufficient to effect binding to an insulin peptide, or a fusion protein comprising a portion of DQ8 sufficient to effect binding to an insulin peptide. The fusion protein may comprise a labeled DQ8. In another preferred embodiment, the class II MHC molecule is DQ8 that has a similar pocket binding region and is associated with celiac disease risk in man (DQ8) or a fragment of DQ8 sufficient to effect binding to a gliadin peptide, or a fusion protein comprising a portion of DQ8 sufficient to effect binding to a gliadin peptide. The fusion protein may comprise a labeled DQ8.

The screening assay can be performed by allowing the class II MHC molecule to interact with an insulin or gliadin peptide, then adding a potential therapeutic agent to be tested. Control reactions will not contain the agent. Following incubation of the reaction mixture under conditions known to be favorable for the association of the MHC molecule and the peptide in the absence of a test agent, the amount of peptide specifically bound to the MHC molecule in the presence of a test agent can be determined. For ease of detecting binding, the peptide can be labeled with a detectable moiety, such as a radionuclide or a fluorescent label, using methods well known in the art. By comparing the amount of specific binding of the peptide and the MHC molecule in the presence of a test agent, as compared to the control level of binding, an agent that increases or decreases the binding of the peptide and class II MHC molecule can be identified. Thus, this drug screening assay provides a rapid and simple method for selecting drugs having a desirable effect on the association of an insulin or gliadin peptide and a MHC molecule.

In one embodiment of the present invention, the monitoring step includes exposure of the DQ8 to a T cell to evaluate the response of the T cell. The T cell may be an in vitro T cell hybridoma population, such as, but not limited to, BDC 12-4.1 and/or BDC 2.5 T cell hybridomas.

In one embodiment, the monitoring of the T cell response reveals a decrease in T cell number or activity following contact with the class II MHC molecule compared to the T cell response seen following contact with the class II MHC molecule in the absence of the potential therapeutic agent, and the potential therapeutic agent is designated as inhibiting the interaction between class II MHC molecules and the insulin (or gliadin) peptides. Such inhibiting agents can inhibit or decrease the progression of an autoimmune disease such as diabetes or celiac disease by enhancing central deletion or altering T cell receptor signaling.

In one embodiment, the drug screening assay can utilize a MHC molecule fusion protein such as a MHC molecule-insulin (or gliadin) peptide fusion protein. The fusion protein is characterized, in part, by eliciting a response from a T cell. Where such a fusion protein is used in the assay, the potential therapeutic agent is selected for its effect on the response from the T cell population, wherein the potential therapeutic agent may enhance or inhibit the response from the T cell population to the fusion protein based on effects imparted by the agent on the fusion protein or the interaction between the fusion protein and the T cells.

Another embodiment of the invention relates to the use of any of the compounds or compositions described herein in the preparation of a medicament for the modulation of an autoimmune disease. The modulation may include the prevention or treatment of an autoimmune disease, such as diabetes and celiac disease, in a mammal.

Each publication or patent cited herein is incorporated herein by reference in its entirety.

Additional objects, advantages, and novel features of this invention will become apparent to those skilled in the art upon examination of the following examples thereof, which are not intended to be limiting.

EXAMPLES

Example 1

Selection of Small Molecule Drug Candidates Directed at DQ8

To identify candidate molecules predicted to bind specific structural pockets of the DQ8 antigen binding groove, a supercomputer was used to screen approximately 140,000 small molecules from the NCI/DTP repository of "drug-like" compounds. Existing crystal structures available for modeling include HLA-DQ8 complexed to insulin B:9-23, PDB code 1JK8. The antigen binding clefts of DQ8 and I-A$^{g7}$ were superimposed, the sites of critical contacts between peptide and MHC were determined, and the atomic coordinates of B:9-23 peptide from the solved crystal structure were displayed with coordinates for the solved crystal structure. To prepare the site for docking, all water molecules were removed and protonation of the residues was done with SYBYL (Tripos). The molecular surface of the structure was explored using sets of spheres to describe potential binding pockets. The sites selected for molecular docking were defined using the SPHGEN program (generates a grid of points that reflect the shape of the selected site) and filtered through CLUSTER. The CLUSTER program groups the selected spheres to define the points that are used by DOCK v5.1.0 to match potential ligand atoms with spheres. Intermolecular AMBER energy scoring (van der Waals+columbic), contact scoring, and bump filtering were implemented in the DOCK program algorithm. The identified orientation and conformation of the insulin B:9-23 peptide was complementary with the antigen binding cleft for the crystal structure. All NCI organic compounds were docked in 1000 orientations using the DOCK program algorithm and scored based on the sum of attractive and repulsive polar and non-polar interactions to compute free energy ($\Delta G$) on binding. The best orientation and scores (contact and electrostatic) were calculated. PYMOL was used to generate molecular graphic images. Table 1 lists top scoring compounds binding the p6 and p4 structural pockets.

TABLE 1

Top scoring small molecules for structural pockets 6 and 4 in the peptide binding grooves in the class II MHC molecule HLA-DQ8.

| Pocket 4 Compounds | Pocket 6 Compounds |
|---|---|
| N-(2-chlorophenyl)dicarbonimido/ic diamide/imido | 1-(2-oxiranylmethyl)-15,3,5,7-tetraazatricyclo[3.3.1.1(3,7)]decane |
| N-(4-(hydroxy(oxido)amino)phenyl)dicarbonimido/ic diamide/imido | 1-(3-chloro-2-propenyl)-15,3,5,7-tetraazatricyclo[3.3.1.1(3,7)]decane |
| 2,2-dihydroxy-N-(2-(trimethyl-5-azanyl)ethyl)hydrazinecarboximidamide | 1-(2,3-dibromo-2-propenyl)-15,3,5,7-tetraazatricyclo[3.3.1.1(3,7)]decane |
| 2,2-dihydroxy-N'-(4-pyridinylmethylene)hydrazinecarboximidohydrazide | 2,3,6,7,10,11-hexahydrotriimidazo[1,2-a: 1,2-c: 1,2-e][1,3,5]triazine |
| 7-methylhexahydro-2,4(1H,3H)-pteridinedione | 1-benzyl-15,3,5,7-tetraazatricyclo[3.3.1.1(3,7)]decane |
| N-(1H-imidazol-1-ylmethyl)-N-methylphenylmethanamine | 1-(2-chloro-2-propenyl)-15,3,5,7-tetraazatricyclo[3.3.1.1(3,7)]decane |
| N-benzyl-N-(1H-imidazol-1-ylmethyl)-N-methylamine | tetradecahydro-2,3-phenazinediamine |
| N-(2-(dimethylamino)ethyl)-2,2-dihydroxyhydrazinecarboximidamide | 1-(4-chloro-2-butenyl)-15,3,5,7-tetraazatricyclo[3.3.1.1(3,7)]decane |
| 2-(((2,2-dihydroxyhydrazino)(imino)methyl)amino)ethyl acetate | 2-amino-N-(3-(dichloromethyl)-5,6,8-trihydroxy-3-methyl-1-oxo-3,4,4a,5,6,7-hexahydro-1H-isochromen-4-yl)propanamide |
| 2-piperazinecarbaldehyde thiosemicarbazone | 2-(15,3,5,7-tetraazatricyclo[3.3.1.1(3,7)]dec-1-yl)ethanol |
| 1,1-bis(2-chloroethyl)hydrazine | 1-bromo-15,3,5,7-tetraazatricyclo[3.3.1.1(3,7)]decane |
| 2,2-dihydroxy-N-(2-((hydroxy(oxido)amino)oxy)ethyl)hydrazinecarboximidamide | 1-(2-(1,3-benzodioxol-5-yl)-1-methylethyl)hydrazine |
| N-(4-chlorophenyl)-2,2-dihydroxyhydrazinecarboximidamide | 1-(2,4,5-trichlorobenzyl)-15,3,5,7-tetraazatricyclo[3.3.1.1(3,7)]decane |
| 1-(2-(15-pyridin-1-yl)ethyl)-15-pyridine | 1-(15,3,5,7-tetraazatricyclo[3.3.1.1(3,7)]dec-1-yl)acetone |
| 3-(3-hydroxy-4-oxo-1(4H)-pyridinyl)alanine | 1-allyl-15,3,5,7-tetraazatricyclo[3.3.1.1(3,7)]decane |
| 2-((2,5-dichlorophenoxy)methyl)-4,5-dihydro-1H-imidazole | 5,6-diamino-1,3-dimethyldihydro-2,4(1H,3H)-pyrimidinedione |
| N'-cyclopentylidene-2,2-dihydroxyhydrazinecarboximidohydrazide | hydroxy(phenyl)methylphosphinic acid |
| N-((2,2-dihydroxyhydrazino)(imino)methyl)benzenesulfonamide | 1,2-dichloro-N1,N1,N1,N1,N2,N2,N2,N2-octamethyl-1,1,2,2-ethanetetramine |
| 2-amino-4-((amino(imino)methyl)amino)butanoic acid | 3-(aminomethyl)-2,4,5,6-tetrachlorobenzylamine |
| N-(3-chloropropyl)-2,2-dihydroxyhydrazinecarboximidamide | 2-(methylthio)-4,6-bis(trimethyl-5-azanyl)pyrimidine |
| N-(2-aminopentanoyl)valine | ethyl 15,4-diazabicyclo[2.2.2]oct-1-ylcarbamate |
| 1-(2-(2-pyridinyl)ethyl)azonane | 2,2'-disulfanediylbis(3-aminopropanoic acid |
| 8-(hydroxy(phenyl)methyl)-9H-purin-6-ol | methyl 4,4-dichloro-2-(1-piperazinyl)-3-butenoate |
| (5-(hydroxy(oxido)amino)-2,4-dioxo-3,4-dihydro-1(2H)-pyrimidinyl)acetaldehyde semicarbazone | N-(aminoacetyl)-4-hydroxyphenylalanine |
| N-(2-cyanoethyl)-2,2-dihydroxyhydrazinecarboximidamide | 1-ethyl-15,3,5,7-tetraazatricyclo[3.3.1.1(3,7)]decane |
| 2,2-dihydroxy-N'-(1-methylethylidene)hydrazinecarboximidohydrazide | 1,4,7-triazacyclotridecane |
| 2,2-dihydroxy-N-(2-(methylsulfonyl)ethyl)hydrazinecarboximidamide | 5,5'-bis(hydroxymethyl)-3,3',5,5'-tetramethyl-3,3'-bimorpholine-2,2'-dione |
| N-(2-bromoethyl)-2,2-dihydroxyhydrazinecarboximidamide | S-((2-amino-2-azetidinyl)methyl)hydrogen thiosulfate |
| N-benzyl-2,2-dihydroxyhydrazinecarboximidamide | 4,4'-(cyclohexane-1,2-diyl)dipiperazine-2,6-dione |
| ((3,4-diamino-4-oxobutyl)thio)acetic acid | 2-methylene-3-phenyl-1-azabicyclo[2.2.2]oct-3-yl propionate |
| 2-amino-1-phenyl-1-butanol | (E)-4,4'-(ethene-1,2-diyl)dibenzimidamide |
| 2,2-dihydroxy-N-(2- | 1-acetyl-3',4',5',6'-tetrahydro-1'H-spiro[indoline-3,2'- |

TABLE 1-continued

Top scoring small molecules for structural pockets 6 and 4 in the
peptide binding grooves in the class II MHC molecule HLA-DQ8.

| Pocket 4 Compounds | Pocket 6 Compounds |
|---|---|
| methoxyethyl)hydrazinecarboximidamide | pyrimidin]-2-one |
| 3,4-dimethyl-5-phenyl-1,3-oxazolidine | 3-phenoxyproline |
| 1-benzyl-3,4-pyrrolidinediol | 1'-acetyl-4-methylspiro[imidazolidine-2,3'-indolin]-2'-one |
| 2,6-diaminoheptanedioic acid | |
| N-butyl-N-methyl-1,3,5-triazatricyclo[3.3.1.1(3,7)]decan-7-amine | |

Example 2

In Vitro Testing of Compounds

This example describes the screening of small molecules predicted to bind to pockets 4 and 6 of human DQ8.

Figure 1A:
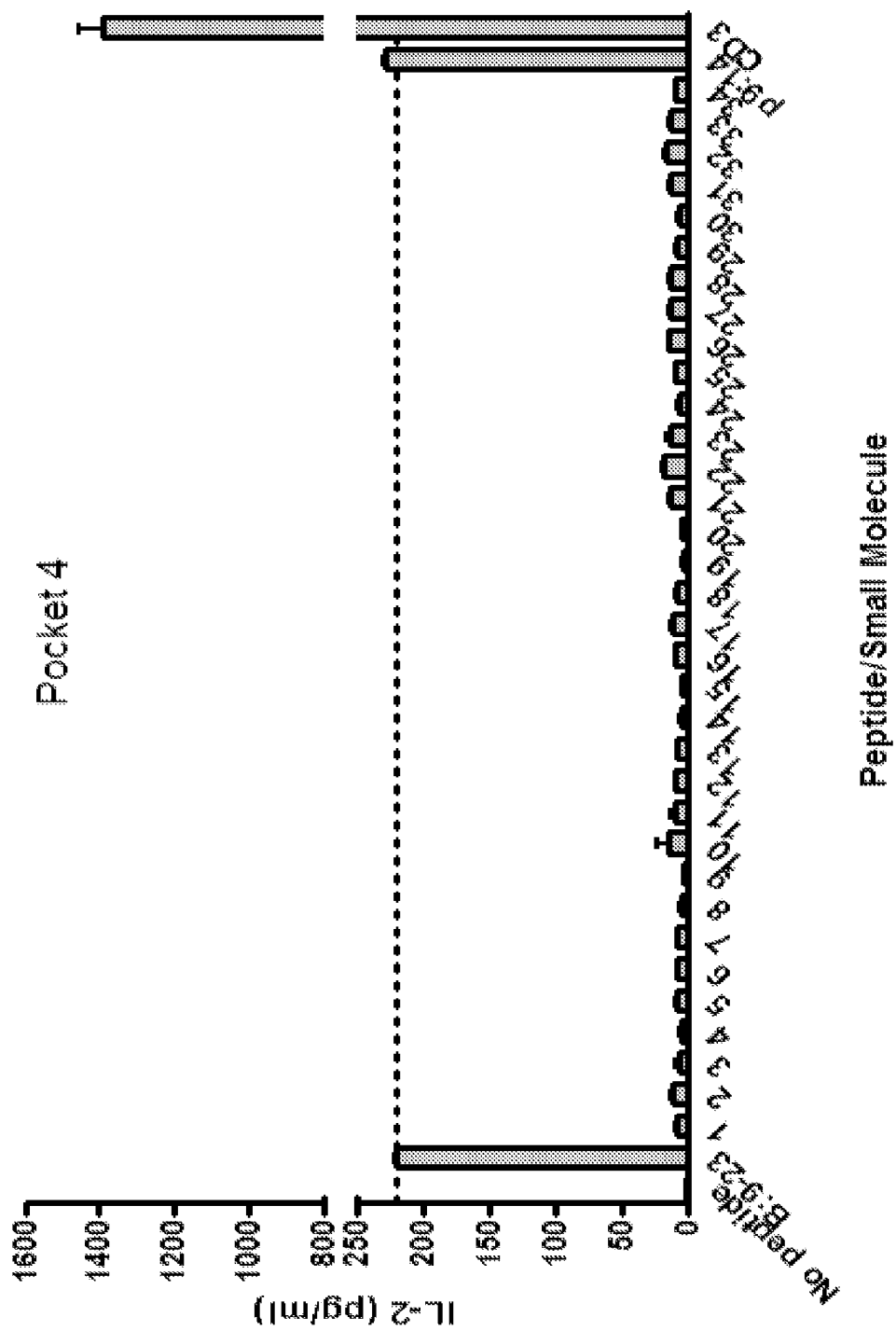
FIGS. 1A and 1B show the screening of small molecules predicted to occupy pockets along the DQ8 binding groove.
Figure 1B:
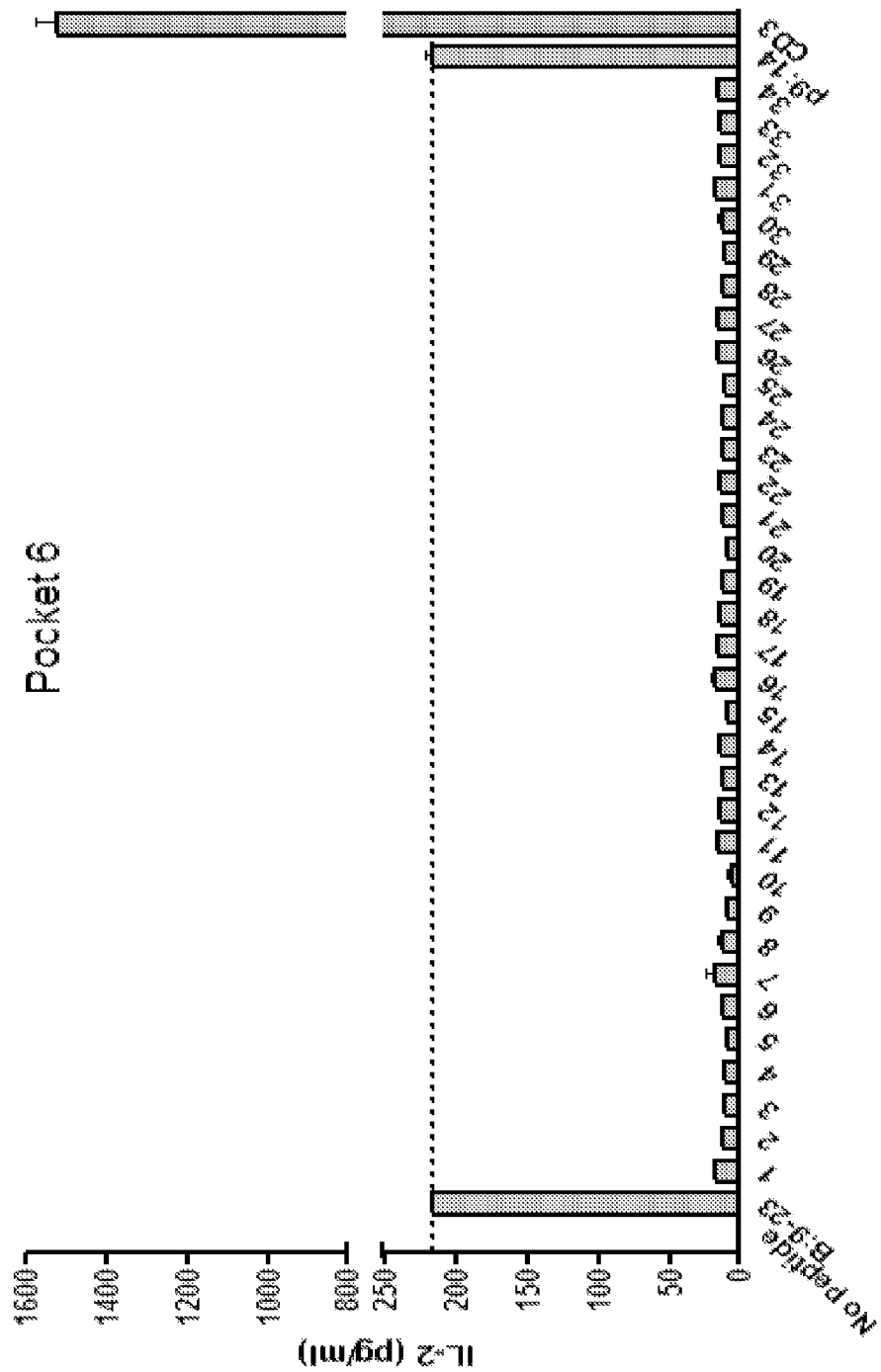

A T cell stimulation assay using the clone 5 T cell hybridoma (a DQ8 restricted T cell that responds to the insulin B chain amino acids 9-23) with insulin B:9-23 peptide and small molecules predicted to bind pocket 4 and pocket 6 was conducted. Results (shown in FIGS. 1A (pocket 4) and 1B (pocket 6)) are provided as IL-2 measured in the tissue culture supernatant after overnight culture. Compound p9:14 (pocket 9:compound 14) was used as a control compound that does not change stimulation to the B:9-23 peptide. Compounds were screened at a concentration of 0.104.

Compounds were tested for their activity in inhibiting the response of multiple anti-B:9-23 TCRs. A T cell stimulation assay was conducted to evaluate the inhibitory activity of the compounds in celiac disease (gluten insensitivity). Using the 489 TCR recognizing gliadin peptide presented by human DQ8, the compounds were tested for their ability to inhibit antigen presentation by human DQ8. FIGS. 2B-2F depict inhibition curves of compounds that block T cell responses to the B:9-23 peptide. Three TCRs are depicted; ●8-1.1α1 and ○BDC 12-4.1 recognize insulin B:9-23 peptide, while ■BDC 2.5 responds to a chromogranin mimotope. Percentage of inhibition was calculated from the stimulation of peptide alone for each TCR. Data points represent triplicate wells for each concentration of small molecule with peptide. Inhibition curves are representative of at least 3 independent experiments.

The results of these T cell stimulation assays and competitive binding assays are provided in Table 2, along with the chemical structures of the compounds tested.

| Compound ID | Compound Structure | T cell stimulation Assay Clone 5 & B:9-23 ($IC_{50}$) | Competitive Binding Assay B:9-23 to DQ8 ($IC_{50}$) | T cell stimulation assay 489 TCR & p1E/p9E alpha gliadin ($IC_{50}$) |
|---|---|---|---|---|
| p4:1 | (structure: chlorophenyl biguanide) | <0.0001 uM | >100 uM | <100 uM |
| p4:2 | (structure: 4-nitrophenyl biguanide) | <0.0001 uM | No inhibition | <100 uM |

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p4:3 | 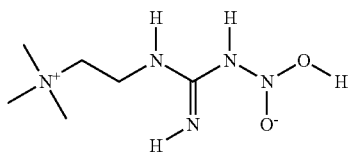 | <0.1 uM | No inhibition | |
| p4:4 | 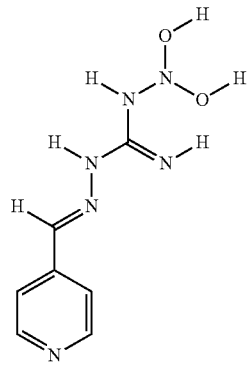 [SMILES: [H]/N=C(/N/N=C/c1ccncc1)NN(O)O] | <0.1 uM | No inhibition | 100 uM |
| p4:5 | 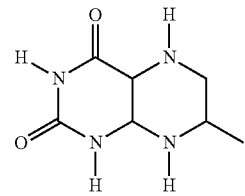 | <0.1 uM | >100 uM | No inhibition |
| p4:6 | 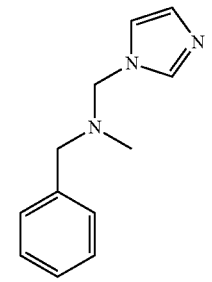 | <0.1 uM | No inhibition | <100 uM |
| p4:7 | 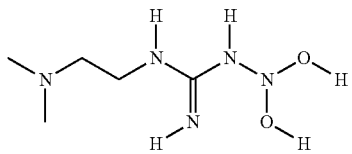 | <0.1 uM | <100 uM | 100 uM |
| p4:8 | 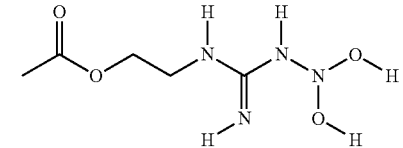 | <0.1 uM | No inhibition | No inhibition |

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p4:9 | 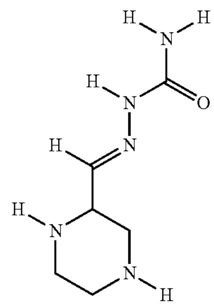 [SMILES: NC(=O)N/N=C/C1CNCCN1] | <0.1 uM | No inhibition | No inhibition |
| p4:10 | 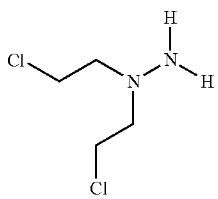 | <0.1 uM | No inhibition | 100 uM |
| p4:11 | 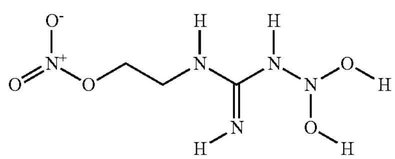 [SMILES: [H]/N=C(\NCCO[N+](=O)[O-])NN(O)O] | <0.1 uM | >100 uM | 100 uM |
| p4:12 | 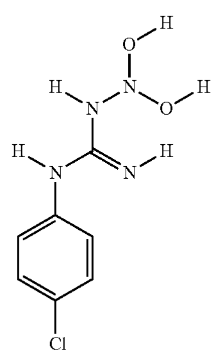 [SMILES: [H]/N=C(/Nc1ccc(Cl)cc1)NN(O)O] | <0.1 uM | >100 uM | <100 uM |
| p4:13 | 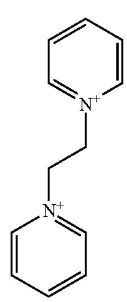 [SMILES: c1cc[n+](CC[n+]2ccccc2)cc1] | <0.1 uM | No inhibition | No inhibition |

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
| --- | --- | --- | --- | --- |
| p4:14 | 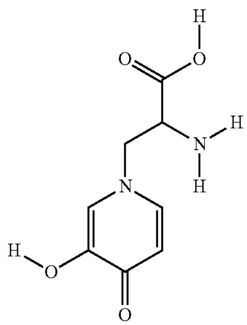 [SMILES: NC(Cn1ccc(=O)c(O)c1)C(=O)O] | <0.1 uM | No inhibition | 100 uM |
| p4:15 | 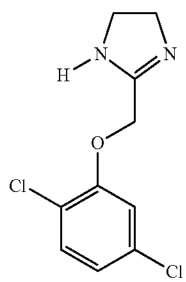 [SMILES: Clc1ccc(Cl)c(OCC2=NCCN2)c1] | <0.1 uM | >100 uM | <100 uM |
| p4:16 | 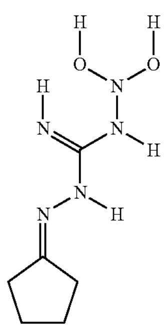 [SMILES: [H]/N=C(/NN=C1CCCC1)NN(O)O] | <0.1 uM | >100 uM | |
| p4:17 | 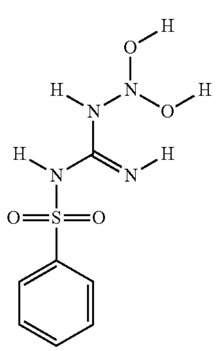 [SMILES: [H]/N=C(\NN(O)O)NS(=O)(=O)c1ccccc1] | <0.1 uM | >100 uM | |
| p4:18 | 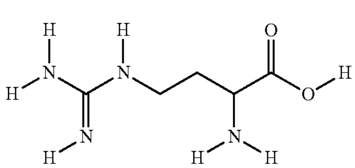 [SMILES: [H]/N=C(\N)NCCC(N)C(=O)O] | <0.1 uM | No inhibition | |

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p4:19 | 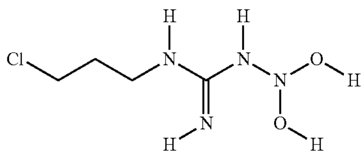 [SMILES: [H]/N=C(\NCCCCl)NN(O)O] | <0.1 uM | >100 uM | |
| p4:20 | 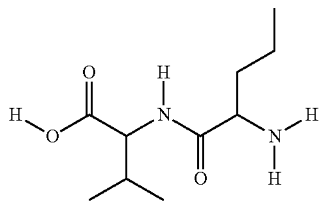 | <0.1 uM | >100 uM | |
| p4:21 | 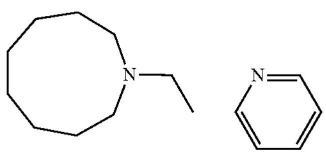 | <0.1 uM | No inhibition | |
| p4:22 | 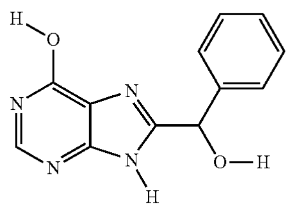 [SMILES: Oc1ncnc2[nH]c(C(O)c3ccccc3)nc12] | <0.1 uM | >100 uM | |
| p4:23 | 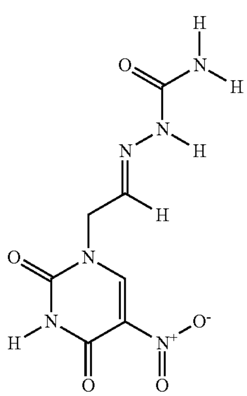 [SMILES: NC(=O)N/N=C/Cn1cc([N+](=O)[O-])c(=O)[nH]c1=O] | <0.1 uM | >100 uM | |
| p4:24 | 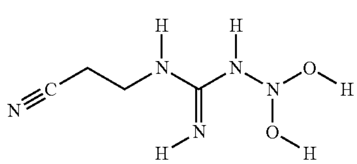 [SMILES: [H]/N=C(\NCCC#N)NN(O)O] | <0.1 uM | No inhibition | |
| p4:25 | 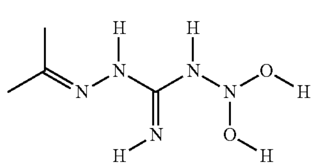 | <0.1 uM | >100 uM | |

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p4:26 | 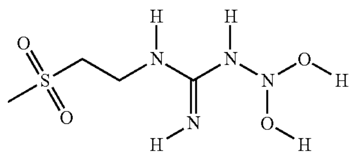 | <0.1 uM | No inhibition | |
| p4:27 | 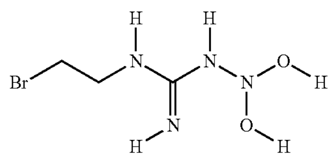 [SMILES: [H]/N=C(\NCCBr)NN(O)O] | <0.1 uM | >100 uM | |
| p4:28 | 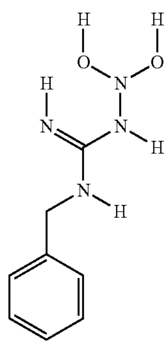 [SMILES: [H]/N=C(/NCc1ccccc1)NN(O)O] | <0.1 uM | >100 uM | |
| p4:29 | 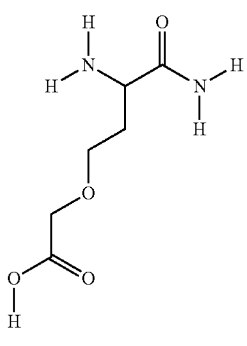 [SMILES: NC(=O)C(N)CCOCC(=O)O] | <0.1 uM | 100 uM | |
| p4:30 | 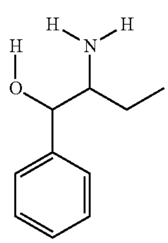 | <0.1 uM | No inhibition | |
| p4:31 | 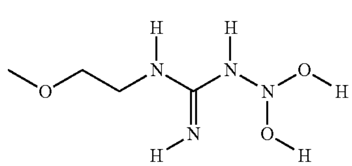 | <0.1 uM | >100 uM | |

-continued

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p4:32 | 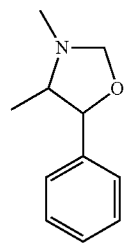 | <0.1 uM | <100 uM | |
| p4:33 | 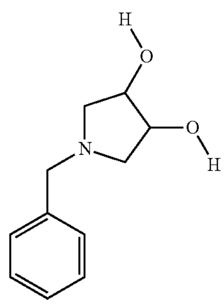 [SMILES: OC1CN(Cc2ccccc2)CC1O] | <0.1 uM | No inhibition | |
| p4:34 | 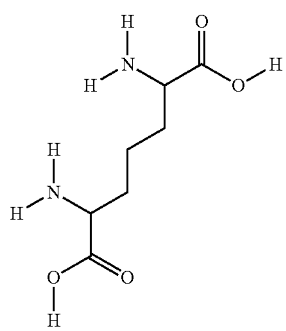 [SMILES: NC(CCCC(N)C(=O)O)C(=O)O] | <0.1 uM | >100 uM | |
| p4:35 | 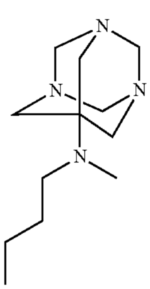 [SMILES: CCCCN(C)C12CN3CN(CN(C3)C1)C2] | <0.1 uM | >100 uM | |
| p6:1 | 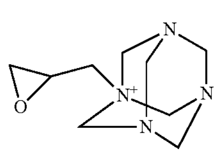 | <0.0001 uM | No inhibition | No inhibition |
| TATD | 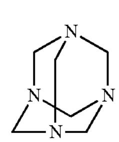 | | 4.5 pM | 20 nM |

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p6:2 | 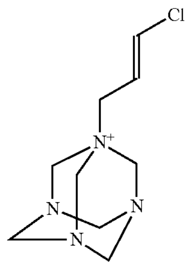 | <0.0001 uM | No inhibition | No inhibition |
| p6:3 | 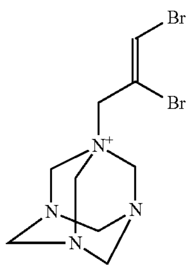 | <0.1 uM | >100 uM | No inhibition |
| p6:4 | 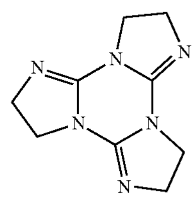 [SMILES: C1CN2C(=N1)N1CCN=C1N1CCN=C21] | <0.1 uM | No inhibition | >100 uM |
| p6:5 | 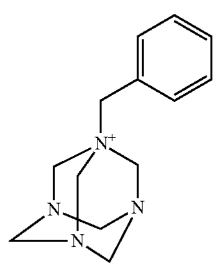 [SMILES: C[N+]1(Cc2ccccc2)CN2CNCN(C2)C1] | <0.1 uM | >100 uM | 0.55 uM |
| p6:6 | 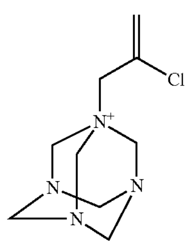 | <0.1 uM | >100 uM | 0.6 uM |
| p6:7 | 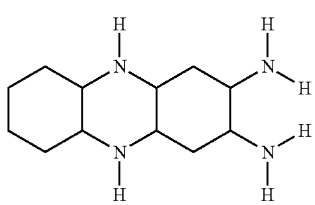 [SMILES: NC1CC2NC3CCCCC3NC2CC1N] | <0.1 uM | No inhibition | 1 uM |

-continued

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p6:8 | (structure) | <0.1 uM | No inhibition | No inhibition |
| p6:9 | (structure) | <0.1 uM | 100 uM | <100 uM |
| p6:10 | (structure) | <0.1 uM | No inhibition | >100 uM |
| p6:11 | (structure) | <0.1 uM | >100 uM | <100 fM |
| p6:12 | (structure) | <0.1 uM | >100 uM | 2 uM |
| p6:13 | (structure) | <0.1 uM | >100 uM | <0.1 uM |

-continued

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p6:14 | 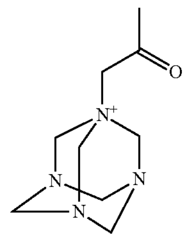 | <0.1 uM | >100 uM | 30 uM |
| p6:15 | 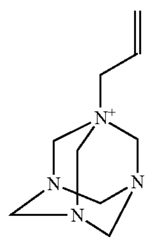 | <0.1 uM | >100 uM | 0.0002 uM |
| p6:16 | 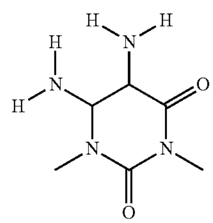 | <0.1 uM | No inhibition | No inhibition |
| p6:17 | 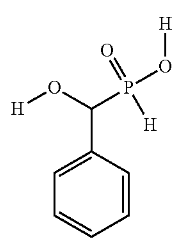 [SMILES: O=[PH](O)C(O)c1ccccc1] | <0.1 uM | >100 uM | No inhibition |
| p6:18 | 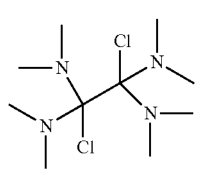 | <0.1 uM | >100 uM | No inhibition |
| p6:19 | 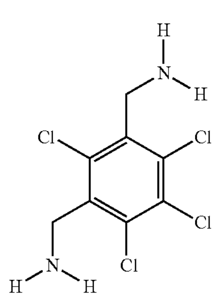 [SMILES: NCc1c(Cl)c(Cl)c(Cl)c(CN)c1Cl] | <0.1 uM | >100 uM | 0.04 uM |

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p6:20 | 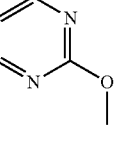 | <0.1 uM | No inhibition | >100 uM |
| p6:21 | 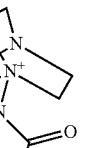 | <0.1 uM | <100 uM | |
| p6:22 | 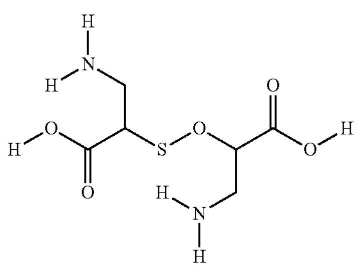 [SMILES: NCC(OSC(CN)C(=O)O)C(=O)O] | <0.1 uM | <100 uM | |
| p6:23 | 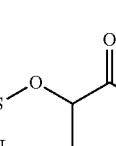 | <0.1 uM | >100 uM | |
| p6:24 | 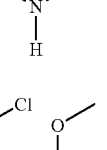 | <0.1 uM | >100 uM | |

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p6:26 | 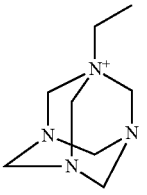 | <0.1 uM | No inhibition | |
| p6:27 | 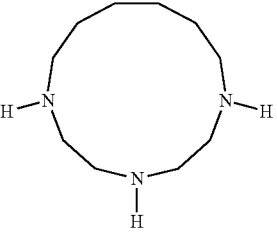 [SMILES: C1CCCNCCNCCNCC1] | <0.1 uM | No inhibition | |
| p6:28 | 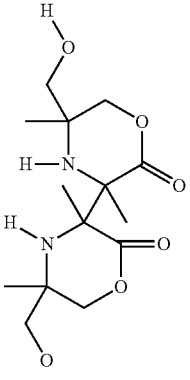 | <0.1 uM | No inhibition | |
| p6:30 | 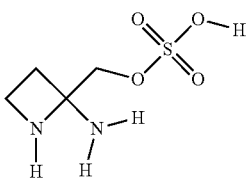 [SMILES: NC1(COS(=O)(=O)O)CCN1] | <0.1 uM | No inhibition | |
| p6:31 | 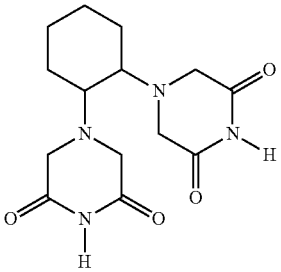 [SMILES: O=C1CN(C2CCCCC2N2CC(=O)NC(=O)C2)CC(=O)N1] | <0.1 uM | No inhibition | |
| p6:32 | 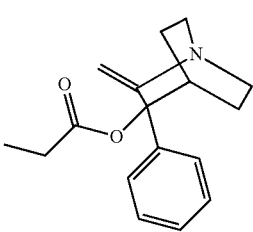 [SMILES: C=CC(OC(=O)CC)(c1ccccc1)C1CCNCC1] | <0.1 uM | No inhibition | 0.45 uM |

| Compound ID | Compound Structure | T cell stimulation Assay Clone 5 & B:9-23 (IC$_{50}$) | Competitive Binding Assay B:9-23 to DQ8 (IC$_{50}$) | T cell stimulation assay 489 TCR & p1E/p9E alpha gliadin (IC$_{50}$) |
|---|---|---|---|---|
| p6:33 | (structure) | <0.1 uM | No inhibition | 0.5 uM |
| p6:34 | (structure) | <0.1 uM | <100 uM | |

Notes:
A blank means that the compound has not been tested.
> 100 uM means there is so some effect when tested at 100 uM but the compound did not inhibit 50%.
< [concentration] means that lower concentrations for a compound have not been used in that assay.

Example 3

Selection of Small Molecule Drug Candidates Directed at I-Ag$^7$

To identify candidate molecules predicted to bind structural pockets 1 and 6 of the I-A$^{g7}$ antigen binding groove, the in silico methodology of Example 1 was used. Table 3 lists NCI identifier the top 40 scoring compounds for each binding pocket.

TABLE 3

Top 40 scoring small molecules for binding pockets 1 and 6 along the I-A$^{g7}$ binding groove.

| Pocket 1 | Pocket 6 |
|---|---|
| 14664 | 163897 |
| 15989 | 177979 |
| 271279 | 172855 |
| 34765 | 4436 |
| 10006 | 281703 |
| 108225 | 177977 |
| 145425 | 168615 |
| 756 | 7308 |
| 401235 | 203305 |
| 67309 | 202406 |
| 382775 | 5062 |
| 93740 | 202028 |
| 17109 | 667746 |
| 79079 | 38241 |
| 116524 | 130818 |

TABLE 3-continued

Top 40 scoring small molecules for binding pockets 1 and 6 along the I-A$^{g7}$ binding groove.

| Pocket 1 | Pocket 6 |
|---|---|
| 62629 | 53040 |
| 223526 | 179805 |
| 344551 | 172826 |
| 140867 | 621512 |
| 23723 | 358064 |
| 36822 | 206142 |
| 30101 | 281218 |
| 110650 | 22037 |
| 760 | 100731 |
| 67203 | 380107 |
| 7368 | 28011 |
| 34766 | 347909 |
| 5377 | 302851 |
| 110649 | 26369 |
| 251037 | 281709 |
| 52758 | 15140 |
| 97090 | 193502 |
| 112525 | 88614 |
| 252063 | 78774 |
| 36172 | 57811 |
| 370387 | 659274 |
| 69211 | 107246 |
| 677504 | 179458 |
| 65007 | 142430 |
| 675585 | 57792 |

Numbers provided in Table 3 are the NCI identifiers which can be used to identify compound formulas, structures, and molecular weights from the National Cancer Institute, Developmental Therapeutics Program (dtp.nci.nih.gov/dtpstandard/dwindex/index.jsp).

Example 4

In Vitro Testing of Compounds

The top 40 scoring compounds for each of pocket 1 and 6, in the in silico study described in Example 3, were screened for their ability to alter anti-B:9-23 T cell responses for three different B:9-23 specific T cell hybridomas (BDC 8-1.1$\alpha_1$, BDC 12-4.1, and BDC 12-4.4). The BDC 8-1.1 alpha$_1$ cell line was produced from splenocytes of a retrogenic mouse with a single 8-1.1 TCR following the procedure used to create BDC 12-4.1 and BDC 12-4.4 T cell hybridomas.

The in vitro T cell stimulation assays utilized hybridomas engineered to produce β-galactosidase following TCR antigen activation (nuclear factor of activated T cell (NFAT) promoter). Small molecules for screening were dissolved in DMSO and diluted in PBS for a final concentration of 0.1% DMSO in each well. Each small molecule was screened at a concentration of 100 μM. Peptides for stimulation were HPLC purified (>95%) and dissolved in sterile lipopolysaccharide free PBS at a neutral pH. Insulin B:9-23 (SHLVEALYLVCGERG (SEQ ID NO:2)) peptide was used at a concentration of 100 μg/m and the BDC 2.5 mimotope (EKAHRPIWARMDAKK (SEQ ID NO:3)) at 20 μg/ml. Anti-I-A$^{g7}$ monoclonal antibodies were used at a concentration of 10 μg/ml. Upon stimulation, LacZ production correlated with IL-2 production.

Figure 3A:
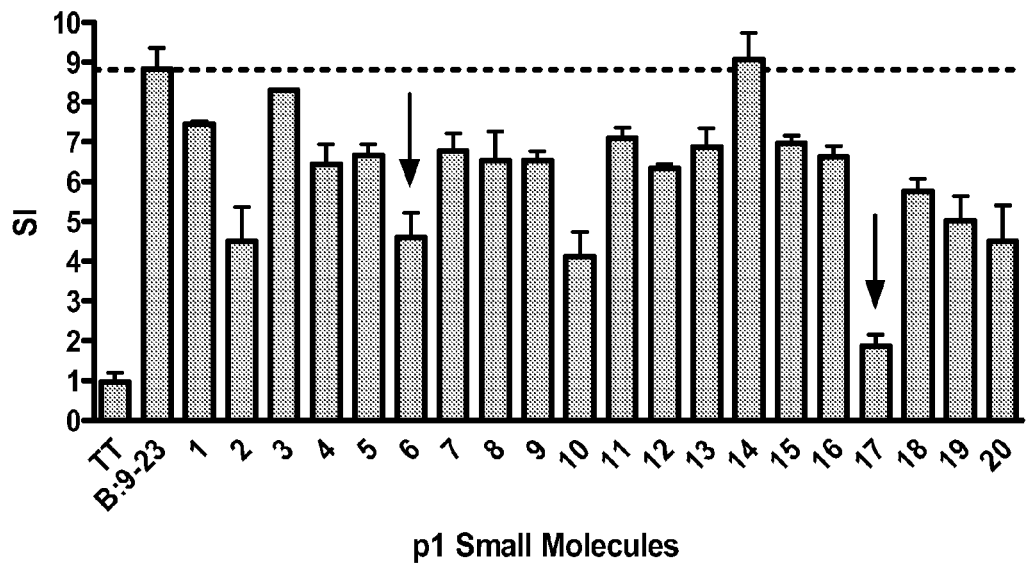
FIG. 3 shows the results of screening the top 40 scoring compounds for each of pocket 1 and 6, for their ability to alter anti-B:9-23 T cell responses for three different B:9-23 specific T cell hybridomas. Pocket 1 results are shown in FIG. 3A and pocket 6 results are shown in FIG. 3B.
Figure 3B:
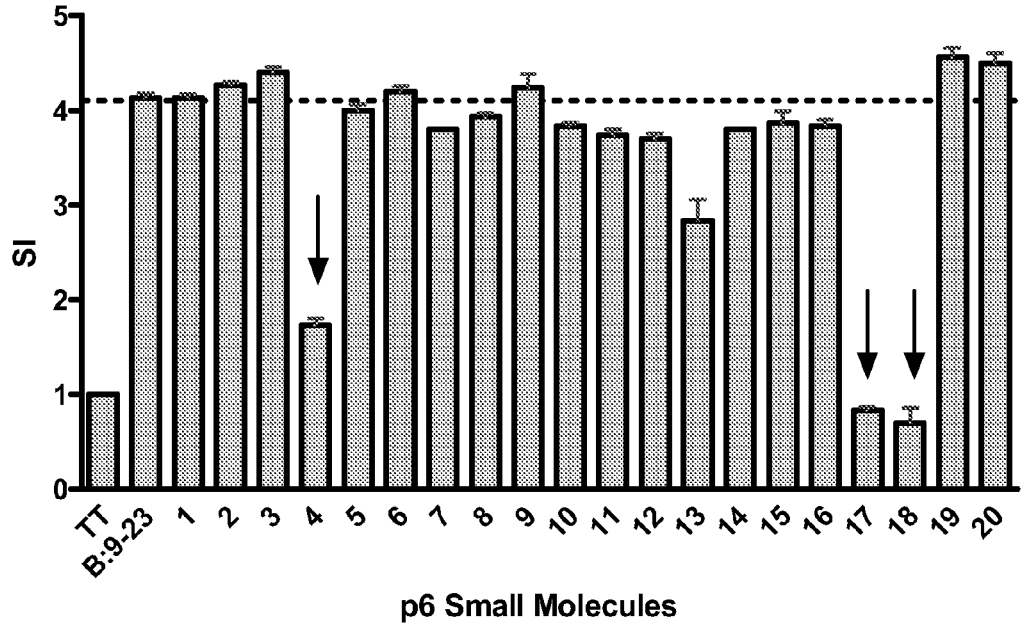

From the top scoring 40 compounds predicted to occupy pockets p1 or p6, a subset resulted in inhibition of B:9-23 TCR activation; 2/40 for p1 and 3/40 for p6 (FIGS. 3A (pocket 1) and 3B (pocket 6), and Table 4).

TABLE 4

Inhibitory compounds for B:9-23 activated TCRs

| Small Molecule | IC$_{50}$ for anti-B:9-23 TCRs | |
|---|---|---|
| | BDC 12-4.1 | 8-1.1$\alpha_1$ |
| S-(2-(dimethylamino)ethyl) hydrogen thiosulfate<br>Pocket 1 | 7.7 μM | 54.7 μM |
| 8-Azaguanine<br>Pocket 1 | 24.0 μM | 25.5 μM |

TABLE 4-continued

Inhibitory compounds for B:9-23 activated TCRs

| Small Molecule | IC$_{50}$ for anti-B:9-23 TCRs | |
|---|---|---|
| | BDC 12-4.1 | 8-1.1$\alpha_1$ |
| 1,3,6,8-Tetraazatricyclo (6.2.1.1(3,6))dodecane<br>Pocket 6 | 2.8 μM | 48.8 μM |
| [1,3]dithiolo[4,5-b] quinoxaline-2,2-diamine<br>Pocket 6 | 14.8 μM | 70.4 μM |
| 9-thia-1,3,6,8-tetraazatricyclo[4.3.1.1~3,8~] undecane 9,9-dioxide<br>Pocket 6 | 0.5 μM | 28.4 μM |

Example 5

Figure 4A:
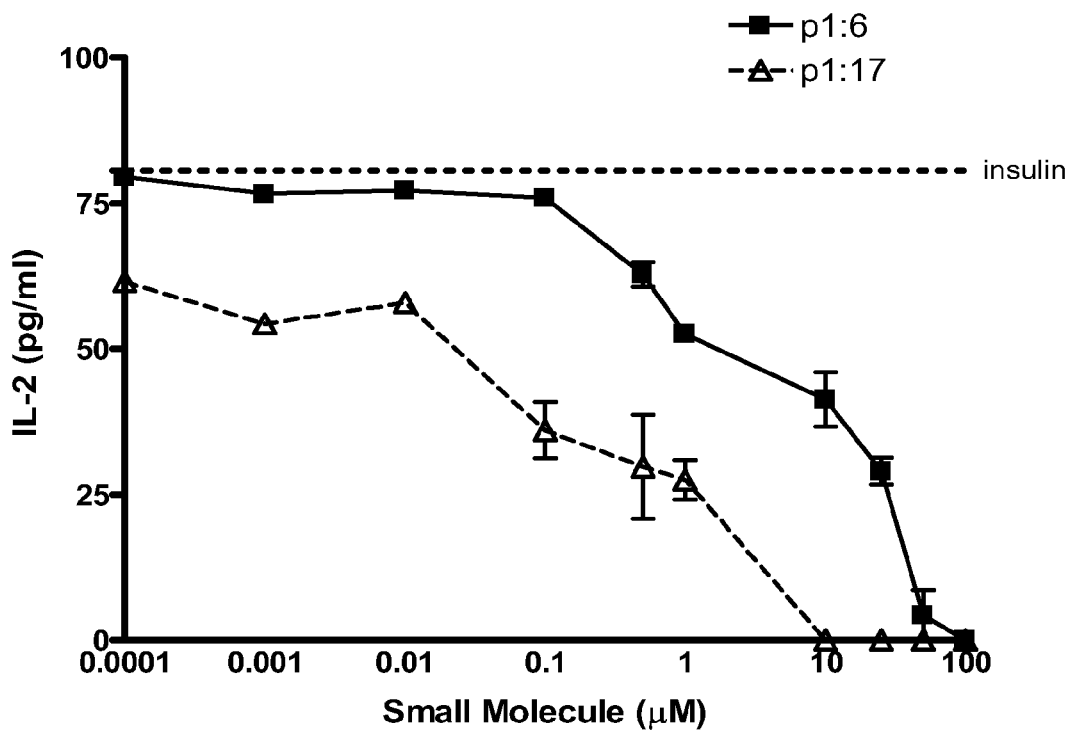
FIGS. 4A-4C show the $IC_{50}$ values for small molecules p1:17 (pocket 1: compound 17), p6:4, and p6:18.
Figure 4B:
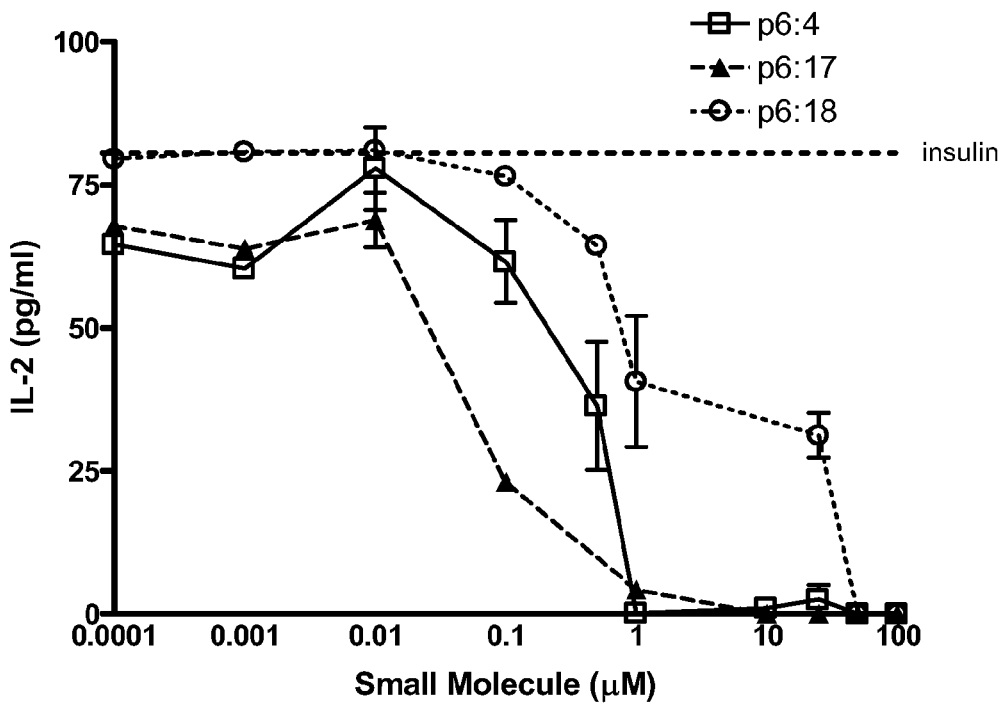
Figure 4C:
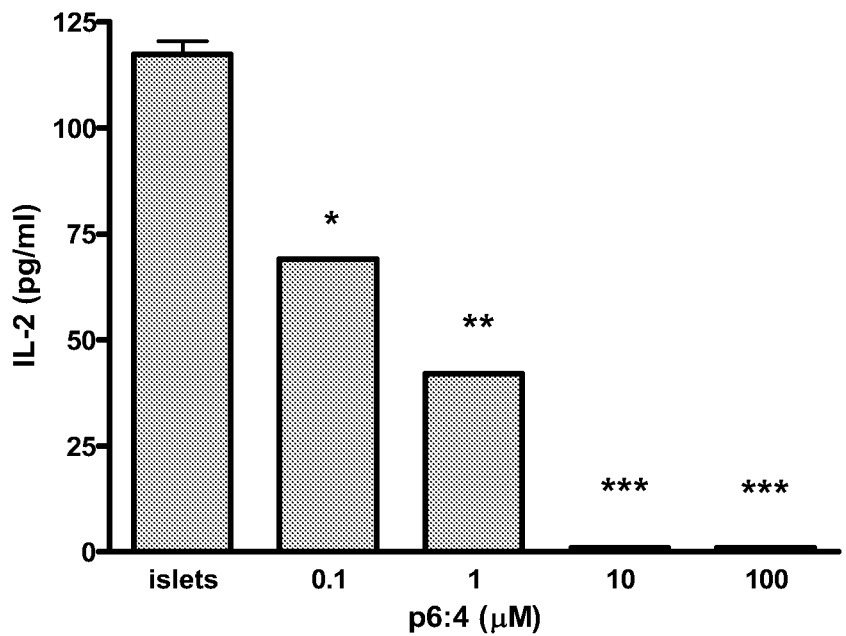
Figure 4D:
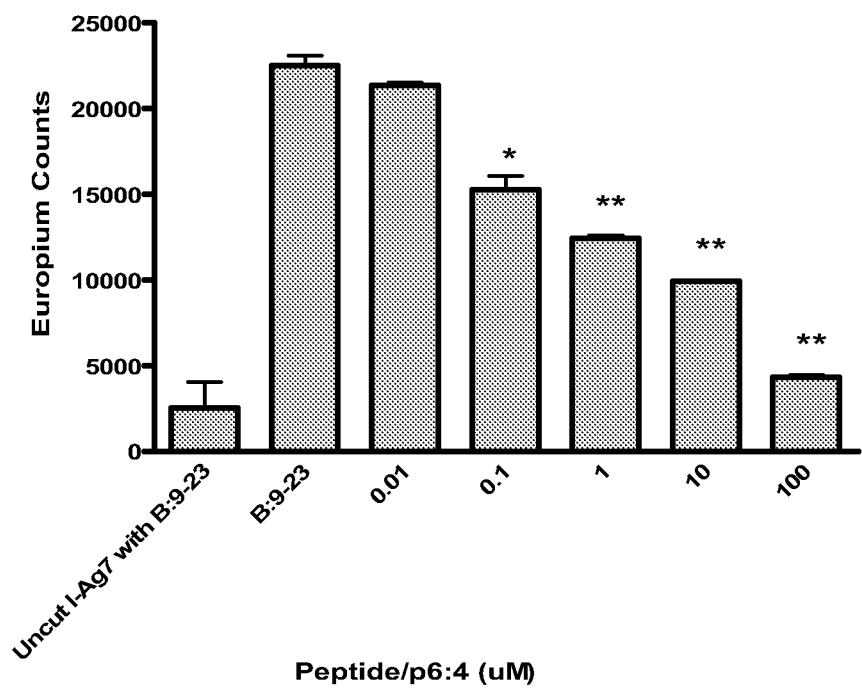
FIG. 4D shows the ability of the p6:4 molecule to inhibit B:9-23 peptide binding to the empty I-A$^{g7}$ in a dose dependent manner.

Small Molecules Inhibit Insulin Presentation and Displace B:9-23 Peptide Binding to I-A$^{g7}$ The ability of the small molecules to block endogenous insulin presentation was tested. Incubation of whole insulin with I-A$^{g7}$ containing splenocytes activates 5KC cells (T cell hybridoma lacking endogenous TCRα and β chains) transduced with a 4-8 TCR. The small molecules examined were able to block T cell stimulation from endogenously processed insulin, with the small molecules p1:17 (pocket 1: compound 17), p6:4, and p6:18 having IC$_{50}$ values in low nanomolar concentrations (FIGS. 4A and 4B). The p6:4 molecule, tetraazatricyclododecane, was studied in additional detail due to lower IC$_{50}$ values and was able to inhibit TCR response to isolated whole islets from an adult non-diabetic NOD mouse (FIG. 4C), which have been shown to contain dendritic cells with insulin peptides, notably B:9-23. To document direct effects of these small molecules on inhibiting peptide binding to I-A$^{g7}$, an I-A$^{g7}$ protein construct was expressed in baculovirus with a linked peptide. The flexible linker contained a thrombin cleavage site, allowing for thrombin cleavage of the linker and release of the peptide. Performing a soluble binding assay, the p6:4 molecule was able to inhibit B:9-23 peptide binding to the empty I-A$^{g7}$ in a dose dependent manner (FIG. 4D).

To test whether these inhibitory small molecules enhance TCR reactivity selectively to B:9-23 insulin peptides, a chromogranin peptide mimotope presented by I-A$^{g7}$ to the BDC 2.5 T cell hybridoma was studied. Two of the five compounds tested, p1:6 and p6:17, showed no inhibition of chromogranin presentation to the BDC 2.5 hybridoma, while the other three compounds inhibited both B:9-23 and chromogranin presentation to their respective hybridomas. Other compounds predicted to bind pocket 1 and 6 blocked TCR responses, but not all of these molecules were specific for the B:9-23 peptide. Taken together, these data demonstrate that in vitro small molecules are able to inhibit endogenous insulin presentation, displace B:9-23 peptide binding to I-A$^{g7}$, and certain small molecules have specificity for inhibiting insulin presentation to T cells.

Example 6

The Small Molecule, 1,3,6,8-Tetraazatricyclo (6.2.1.1(3,6)) Dodecane, Also Binds to Human DQ8

There is significant homology between the high risk class II allele DQ8 of humans (DQA1*0301-DQB1*0302) and I-A$^{g7}$ of mouse. Furthermore, the amino acid sequences of the murine insulin 2 B:9-23 is identical to human B:9-23. The in silico molecular docking was performed using the compounds from the NCI/DTP repository for pockets along the p1, p6 and p9 binding grooves of DQ8. Twenty out of the top 40 scoring compounds for both pocket 6 of I-A$^{g7}$ and DQ8 were identical, suggesting that small molecules targeted to I-A$^{g7}$ may similarly bind to DQ8 (for p1 0/40 and p9 6/40 are identical).

Figure 4E:
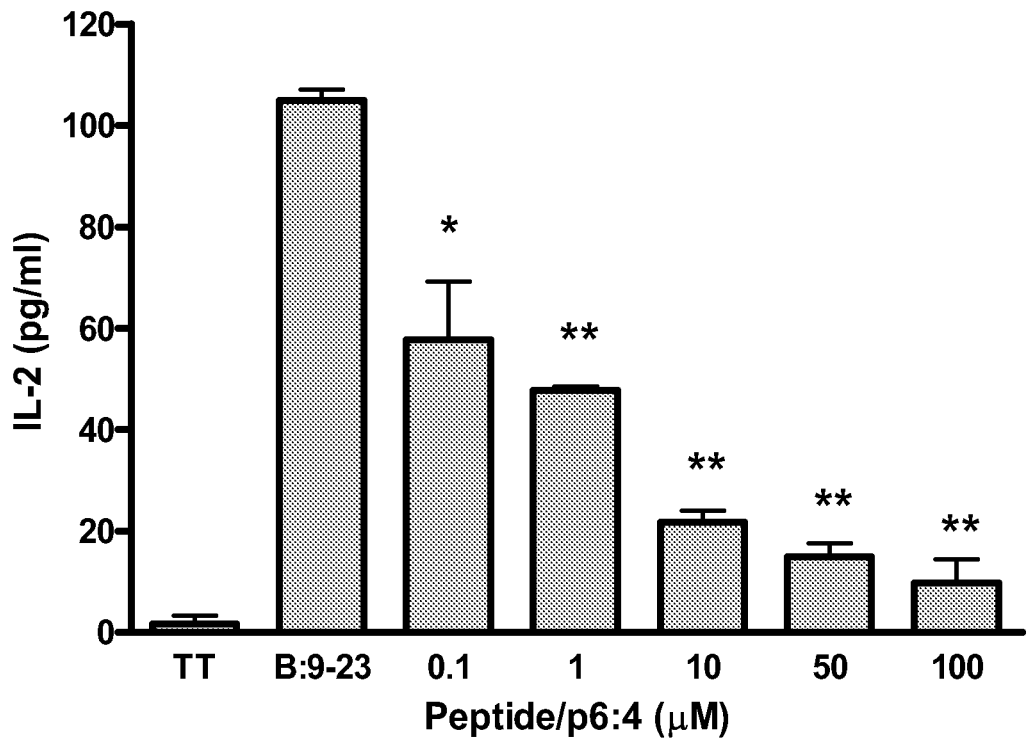
FIG. 4E shows the inhibition of TCR activation by the p6:4 molecule.

The p6:4 molecule was evaluated for the ability to block of B:9-23 peptide presentation by DQ8. Using a TCR sequence obtained from a T cell line generated from the peripheral blood of a diabetic individual with DQ8 molecule, a TCR was identified that is DQ8 restricted and responds to the insulin B:9-23 peptide. Using this TCR along with DQ8 splenocytes from a humanized mouse, the p6:4 molecule was found to inhibit TCR activation (FIG. 4E), suggesting that small molecules targeted to pocket 6 of I-A$^{g7}$ also bind in a similar manner to the human homologue DQ8.

These results demonstrate that the combination of structure guided virtual screening and the concept that small molecules targeted to specific MHC pockets can be immunomodulatory has broad relevance to the prevention and treatment of autoimmunity, such as diabetes.

Example 7

Figure 5A:
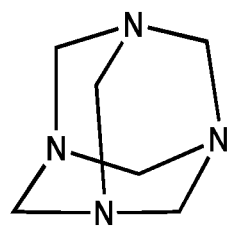
FIG. 5A shows the molecular structure of 1,3,6,8-Tetraazatricyclo (4.4.1.1(3,8)) dodecane, an isomer of the p6:4 molecule.
Figure 5C:
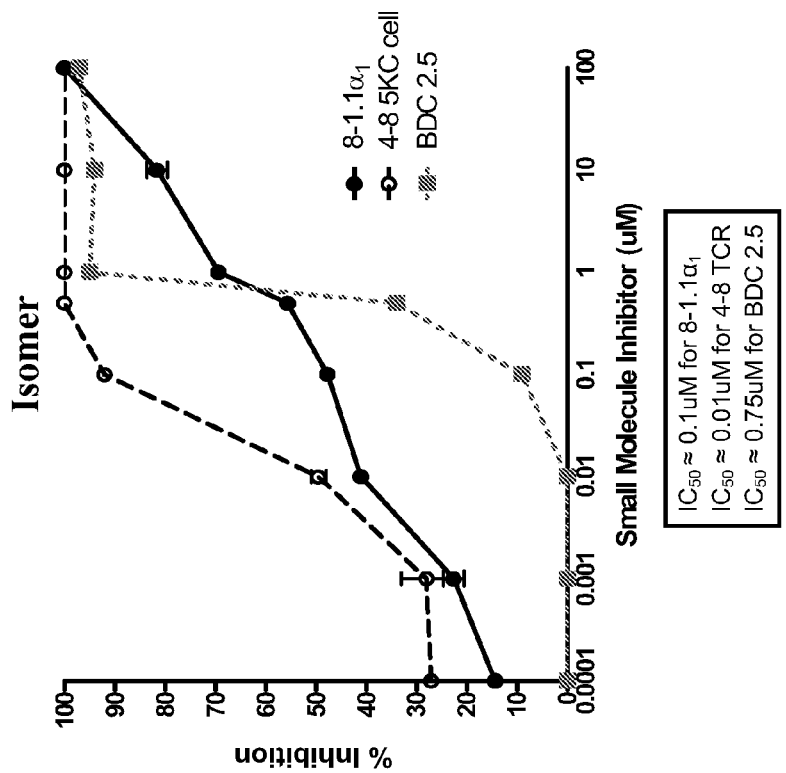
FIGS. 5B and 5C show the inhibition of T cell responses to the autoantigen, amino acids 9-23 in the B chain of insulin, by the p6:4 molecule and its isomer, respectively.
Figure 5B:
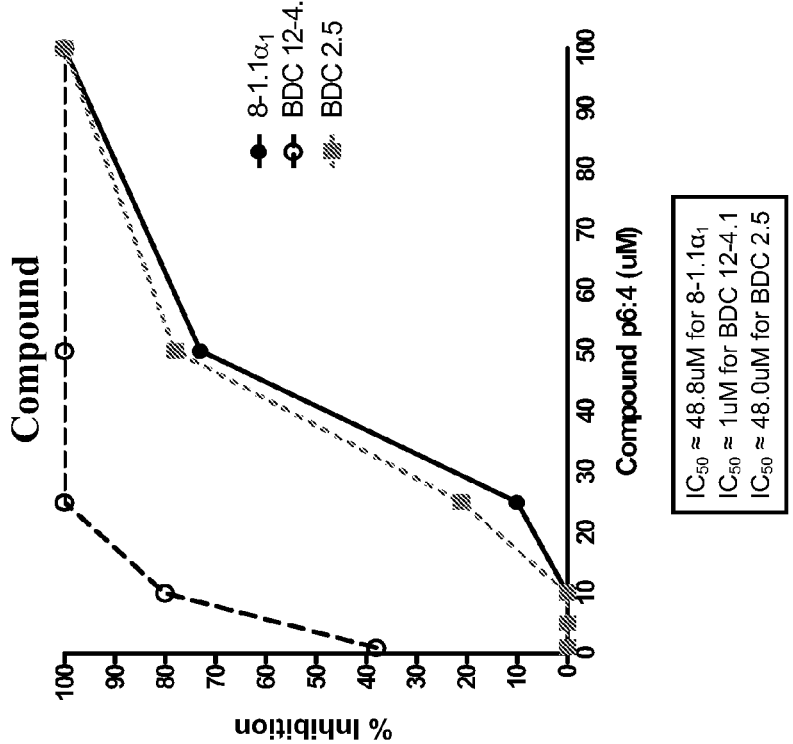
Figure 6A:
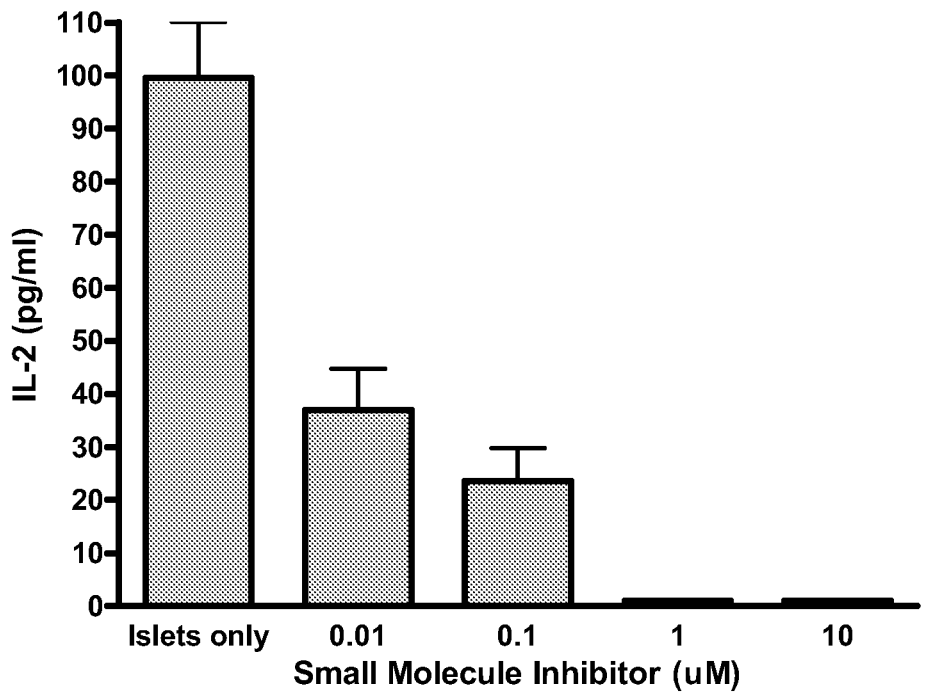
FIGS. 6A and 6B show the ability of the isomer of FIG. 5A to inhibit endogenous antigen presentation of whole insulin by antigen presenting cells, and by islets containing beta cells, respectively.
Figure 6B:
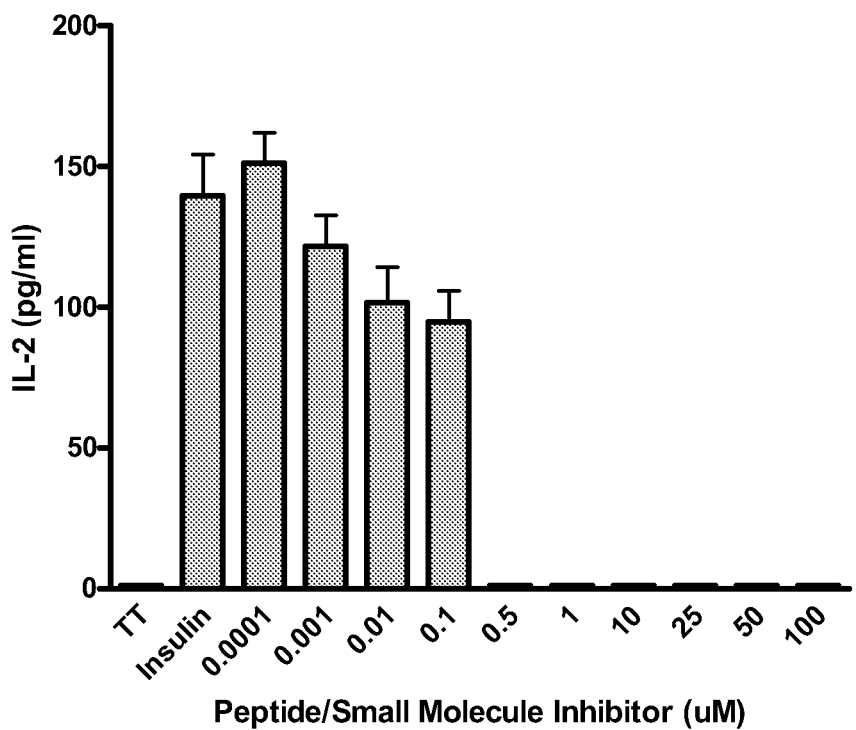

The Molecule 1,3,6,8-Tetraazatricyclo(4.4.1.1(3,8)) Dodecane, Isomer of 1,3,6,8-Tetraazatricyclo (6.2.1.1(3,6)) Dodecane, is Capable of Inhibiting Antigen Presentation by I-Ag7 in Mouse and DQ8 in Humans The small molecule 1,3,6,8-Tetraazatricyclo (4.4.1.1(3, 8)) dodecane (structure shown in FIG. 5A) is an isomer of the molecule p6:4. This molecule inhibited the insulin presentation to T cells capable of causing diabetes in mice and T cells responding to insulin in humans. This compound was able to inhibit T cell response to the autoantigen, amino acids 9-23 in the B chain of insulin, at low nanomolar concentrations (compare FIGS. 5B and 5C). Furthermore, the molecule was able to inhibit endogenous antigen presentation of whole insulin by antigen presenting cells and islets containing beta cells (FIGS. 6A and 6B). Specificity was shown by using the molecule to inhibit tetramer binding (I-A$^{g7}$ complexed to insulin peptides) to T cells. 1,3,6,8-Tetraazatricyclo (4.4.1.1(3,8)) inhibited tetramer staining of T cells recognizing insulin B:9-23 presented by I-A$^{g7}$. In the presence of another tetramer with a different class II presenting molecule (I-A$^b$ complexed to a 3K peptide), the small molecule did not alter T cell staining 1,3,6,8-Tetraazatricyclo (4.4.1.1(3,8)) dodecane did not inhibit antigen presentation by other MHC class II molecules (i.e., no change in tetramer staining of T cells) indicating that it is specific for I-A$^{g7}$.

Figure 7:
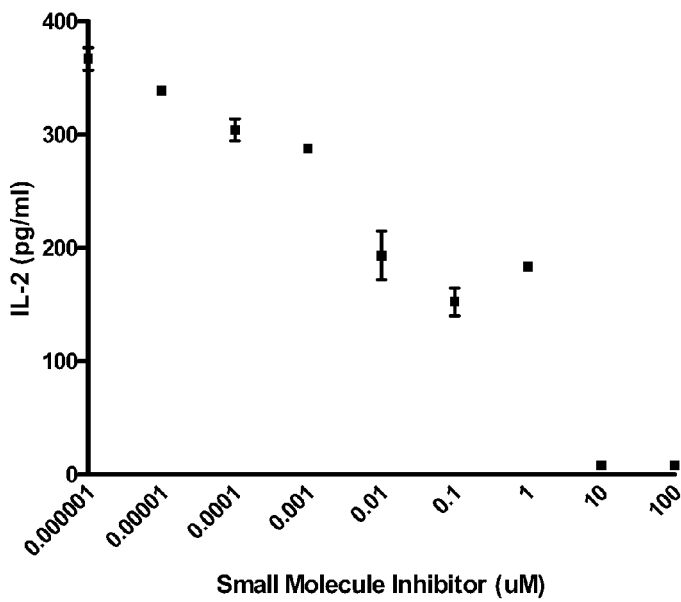
FIG. 7 shows the inhibition of a human T cell receptor recognizing insulin B:9-23 presented by human DQ8 by the isomer of FIG. 5A.
Figure 8:
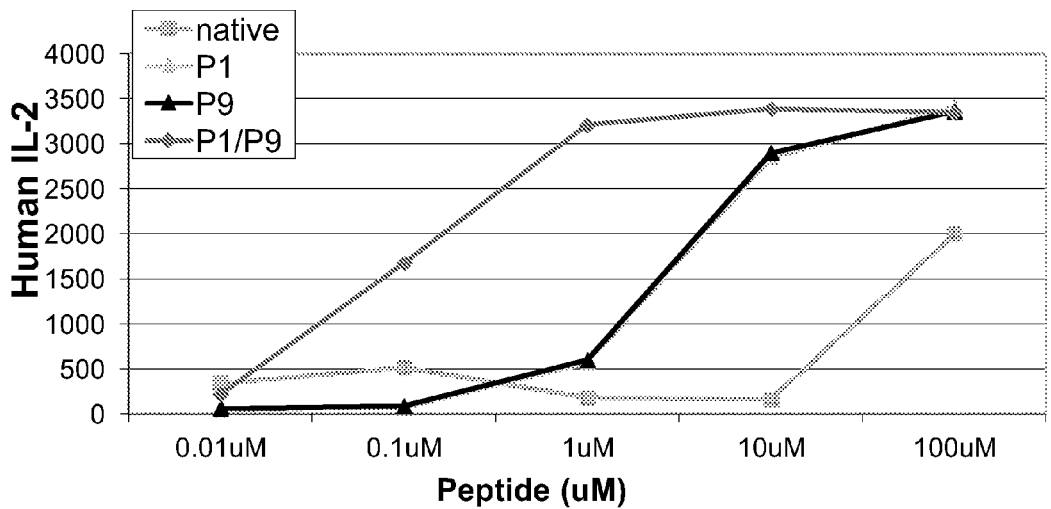
FIG. 8 shows the inhibition of 489 TCR recognizing gliadin peptide presented by human DQ8. For these studies, 50,000 Transduced Jurkat Cells and 50,000 DQ8-Priess Cells were used. The alpha-gliadin peptide used for stimulation is.

1,3,6,8-Tetraazatricyclo (4.4.1.1(3,8)) dodecane was tested with human T cells involved in type 1 diabetes and celiac disease (gluten insensitivity) and was able to inhibit antigen presentation by human DQ8 to these T cells at low nanomolar concentrations. This compound inhibited a human T cell receptor recognizing insulin B:9-23 presented by human DQ8 (FIG. 7), as well as 489 TCR recognizing gliadin peptide presented by human DQ8 (FIG. 8).

Example 8

Identification of Small Molecule Drug Candidates Directed at Pocket 1 and Pocket 9 of Human DQ8

Molecules predicted to occupy pockets 1 and 9 of the human DQ8 peptide binding groove were identified using in silico molecular docking program. The top scoring compounds for each pocket were screened for their ability to inhibit anti-B:9-23 T cell responses. FIGS. 9A and 9B represent the results of the T cell stimulation assay for compounds occupying pocket 1 and pocket 9 of the human DQ8 peptide binding groove, respectively.

For pocket 1, molecules p1:4, p1:12, p1:16, p1:18, p1:21, p1:22 and p1:25 were able to inhibit human T cell receptor recognition of insulin B:9-23 presented by human DQ8 (dotted lines are at the stimulation index of the B:9-23 peptide in the given experiment). The identity of these molecules is as follows:

p1:4: 4,5-dihydroxy-3-nitroso-2,7-naphthalenedisulfonic acid;
p1:12: 5-bromo-3-cyclohexyl-2-hydroxybenzamide, CAS#: 6284-50-0;
p1:16, (2,4-diiodophenoxy)acetic acid (ACD/Name 4.0) CAS#: 77228-65-0;
p1:18, 5-chloro-2-(2-methoxy-2-oxoethoxy) benzoic acid;
p1:21, 5-((2,5-dichloro-4-(hydroxy(oxido)amino)phenyl)diazenyl)-2-imino-4-methyl-2,3-dihydro-1,3-thiazole, CAS#: 33175-12-1;
p1:22: 7-methoxy-10H-pyrido[2,3-b]pyrimido[4,5-e][1,4] thiazine-2,4-diamine CAS#: 42362-20-9; and, p1:25: 2-amino-4-hydroxy-6-mercapto-7-pteridine carboxylic acid.

The small molecules p1:4, p1:12 and p1:16 were studied in additional detail. These molecules exhibited inhibition at nanomolar concentrations (FIG. 10A) but did not change response to CD3-stimulated T cell hybridomas (FIG. 10B).

For pocket 9, molecules p9:1, p9:5, p9:10, p9:17, p9:23 and p9:35 were able to inhibit human T cell receptor recognition of insulin B:9-23 presented by human DQ8. The identity of these molecules is as follows:

p9:1: 3-phosphonopropylphosphonic acid CAS#: 7702-51-4;
p9:5: 3-(carboxymethoxy)-6-oxo-3,6-dihydro-1(2H)-pyridazinyl acetic acid;
p9:10: 1,3-dihydroxy-1,3-propanedisulfonic acid, CAS#: 5450-95-3;
p9:17: 3-deoxy-2,4-dithiopentaric acid, CAS#: 1126-47-2;
p9:23: 2-(1H-tetraazol-5-yl)ethanesulfonic acid;

p9:35: 3-ethylidene-1,2-cyclopropanedicarboxylic acid, CAS#:19257-36-4.

The small molecules p9:5, and p9:23 were studied in additional detail. These molecules were able to exhibit inhibition at nanomolar concentrations (FIG. 11).

Example 9

Prevention or Delay of Insulin Autoantibody Production and Diabetes Onset in NOD Mice A lead candidate small molecule, tetraazatricyclododecane (TATD; 1,3,6,8-tetraazatricyclo (4.4.1.1(3,8)) dodecane), predicted to occupy pocket 6 of the DQ8 molecule, was demonstrated to inhibit T cell response to the insulin B:9-23 peptide presented by I-A$^{g7}$ and DQ8, and block peptide binding to both molecules, with excellent potency. $IC_{50}$ values for two DQ8 restricted T cells are 4.5 pM for clone 5 (insulin B:13-23 restricted) and 20 nM for the 489 TCR (α-gliadin restricted).

To test the efficacy of this molecule in vivo, Jackson NOD mice were treated with TATD at a dose of 20 mg/kg IP daily starting at 4 weeks of age. Treatment ceased at 12 weeks of age. Insulin autoantibody (IAA) was measured before treatment at 8, 10, 12, 16, 20, and 24 weeks of age. Monitoring of peak IAA titers up to 24 weeks of age demonstrated that TATD blocks IAA formation in NOD mice and prevents diabetes onset (FIGS. 12A and 12B). FIG. 12A shows lower peak IAA indices from treated mice compared to controls (p=0.03 comparing the TATD cohort to controls using a paired t-test). FIG. 12B is a life table showing the diabetes incidence of treated (n=10) and control (n=13) mice, and demonstrates that TATD prevents or delays diabetes onset in NOD mice when administered from 4 to 12 weeks of age (p=0.04 comparing treated to control mice).

Example 10

In Vivo Preclinical Therapeutic Evaluation of TATD in DQ8 Humanized Mice

TATD was further evaluated in humanized DQ8 mice. These mice are on a NOD background, I-A null, and contain transgenes for DQ8 and human CD4 (NOD, I-A$^{g7}$ null, DQ8 transgene, Rag KO). TATD was used to develop a rapid ex vivo biomarker assay to monitor the effects of small molecules on antigen presentation in DQ8 humanized mice. To identify a biomarker, mice were treated in vivo with TATD (either by intraperitoneal injection or gastric gavage) and isolated splenocytes or peripheral blood mononuclear cells (PBMCs) were used to monitor antigen presentation to DQ8 restricted T cell receptor (TCR) transfectomas.

Using this biomarker assay, DQ8 humanized mice were treated with a single intraperitoneal dose of TATD (20 mg/kg) and then sacrificed 2 hours later. Splenocytes from treated mice were cultured with the insulin B:13-23 antigen in the presence of clone 5 TCR transfectomas, or deamidated α-gliadin in the presence of the 489 TCR transfectoma. No TATD was added in vitro to the stimulation assays. Control mice received IP injections of PBS (the vehicle in which TATD is dissolved).

The IL-2 response from the TCR transfectomas using splenocytes harvested within 2 hours from TATD treated mice was abrogated compared to PBS treated controls (FIGS. 13A and 13B). Anti-CD3 stimulation was not inhibited in the presence of TATD. Furthermore, a single dose of TATD has effects on antigen presentation out to 7 days and TATD is orally absorbed as gastric gavage of the compound is effective at blocking IL-2 production from the TCR transfectomas.

Pooled PBMCs from TATD treated mice showed similar effects on IL-2 production inhibiting both TCR transfectomas. Clone 5 responds to insulin B:13-23 presented by PBMCs and this response is blocked with in vivo TATD treatment (FIG. 13C), and the same response is seen for deamidated α-gliadin presented by PBMCs to the 489 TCR transfectoma (FIG. 13D).

These studies demonstrate that the degree of MHC restricted T cell recognition of specific autoantigen peptides (insulin B:13-23 peptide and deamidated α-gliadin) defines a measureable biomarker for TATD.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method of preventing, treating or ameliorating autoimmune diabetes by administering to a mammal in need of such treatment, a therapeutically effective amount of a compound selected from the group consisting of:

1,3,6,8-tetraazatricyclo[4.4.1.1(3,8)]dodecane,
1-ethyl-15,3,5,7-tetraazatricyclo[3.3.1.1(3,7)]decane,
1-allyl-15,3,5,7-tetraazatricyclo[3.3.1.1(3,7)]decane,
1-(15,3,5,7-tetraazatricyclo[3.3.1.1(3,7)]dec-1-yl)acetone,
1-(2,4,5-trichlorobenzyl)-15,3,5,7-tetraazatricyclo[3.3.1.1(3,7)]decane,
1-bromo-15,3,5,7-tetraazatricyclo[3.3.1.1(3,7)]decane,
2-(15,3,5,7-tetraazatricyclo[3.3.1.1(3,7)]dec-1-yl)ethanol,
1-(4-chloro-2-butenyl)-15,3,5,7-tetraazatricyclo[3.3.1.1(3,7)]decane,
1-(2-chloro-2-propenyl)-15,3,5,7-tetraazatricyclo[3.3.1.1(3,7)]decane,
1-benzyl-15,3,5,7-tetraazatricyclo[3.3.1.1(3,7)]decane,
1-(2,3-dibromo-2-propenyl)-15,3,5,7-tetraazatricyclo[3.3.1.1(3,7)]decane,
1-(3-chloro-2-propenyl)-15,3,5,7-tetraazatricyclo[3.3.1.1(3,7)]decane, and
1-(2-oxiranylmethyl)-15,3,5,7-tetraazatricyclo[3.3.1.1(3,7)]decane,
and pharmaceutically-acceptable salts thereof.

2. A method of treating autoimmune diabetes, or ameliorating symptoms of autoimmune diabetes, comprising administering to a mammal in need of such treatment a therapeutically effective amount of a combination of at least one of the compounds of claim 1 and one or more other known anti-diabetic or anti-inflammatory or anti-celiac disease compounds.

3. The method of claim 2, wherein the other anti-diabetic compound is at least one of an alpha-glucosidase inhibitor, a biguanide, a Dpp-4 inhibitor, a meglitinide, a sulfonylurea, a thiazolidinedione or combinations thereof.

* * * * *